United States Patent [19]

Yamaguchi et al.

[11] 4,412,289

[45] Oct. 25, 1983

[54] RECONSTRUCTION METHOD OF X-RAY COMPUTED TOMOGRAPHY

[75] Inventors: Shoichiro Yamaguchi; Fujio Kabayashi, both of Tokyo, Japan

[73] Assignee: The President of Tokyo Institute of Technology, Tokyo, Japan

[21] Appl. No.: 227,683

[22] Filed: Jan. 23, 1981

[30] Foreign Application Priority Data

| Feb. 13, 1980 | [JP] | Japan | 55-16340 |
| Mar. 4, 1980 | [JP] | Japan | 55-27168 |
| Mar. 7, 1980 | [JP] | Japan | 55-29446 |
| Mar. 7, 1980 | [JP] | Japan | 55-29447 |

[51] Int. Cl.$^3$ .................... G06F 15/42; G01T 1/20
[52] U.S. Cl. ............................. 364/414; 378/901
[58] Field of Search ............ 364/414, 515; 378/4, 378/11, 12, 901

[56] References Cited

U.S. PATENT DOCUMENTS

| 4,052,619 | 10/1977 | Housfield | 364/414 |
| 4,099,060 | 7/1978 | Franke | 378/11 |
| 4,222,104 | 9/1980 | Moore | 364/414 |
| 4,233,662 | 11/1980 | Lemay | 364/414 |
| 4,266,136 | 5/1981 | Duinker | 364/414 |
| 4,309,614 | 1/1982 | Wagner | 364/414 |
| 4,313,163 | 1/1982 | Mizutani | 378/901 |

OTHER PUBLICATIONS

IBM Tech. Discl. Bull.-"Analog Reconstruction from X-Ray Projections"; Chang et al., vol. 15, No. 12; May 1973; pp. 3712-3714.
Computerized Tomography, The International Journal of Radiological Diagnosis Using CT Scanners, vol. 2, No. 3, 1978, Pergamon Press.

*Primary Examiner*—Errol A. Krass
*Attorney, Agent, or Firm*—Robert E. Burns; Emmanuel J. Lobato; Bruce L. Adams

[57] ABSTRACT

Measured values are produced from one of a plurality of projectional distributions of X-ray being constituting the major data, other measured values are produced from the remaining projectional distributions of X-ray constituting sub-data, X-ray absorption coefficient for picture elements constituting a tomographic plane is calculated to construct a tomogram of the X-ray tested tissue of body, resulting in that a substantial decrease of the measuring time will decrease exposure time to X-ray and/or enable a clear reconstruction of a moving X-ray tested tissue of a body as well as improve substantially the accuracy of reconstruction.

12 Claims, 15 Drawing Figures

RECONSTRUCTION METHOD OF X-RAY COMPUTED TOMOGRAPHY

DETAILED DESCRIPTION OF THE INVENTION

This invention relates to a reconstruction method of X-ray computed tomography, and more particularly to a method of X-ray computed tomography reconstructed by performing desired data calculation.

In general, there have been widely performed a testing procedures by X-ray for checking the internal structure of a product or a human body in the field of industry and medicine. In view of this fact, X-ray computed tomography (hereinafter abbreviated as "CT") has been extensively developed for realizing devices capable of inspecting the internal structure of products or the human body.

BACKGROUND OF THE INVENTION

In conventional X-ray computed tomography, as shown in FIG. 1 by a solid line, a projectional distribution of X-ray is measured by an X-ray detector. The X-ray beam is projected from X-ray source a toward a tissue of body b. Then, as shown in FIG. 1 by a dotted line, X-ray source a and X-ray detector c are rotated by a desired angle $\alpha$ (for example 1°), and at this position the X-ray beam is projected again toward the body tissue of body b, a projectional distribution of X-rays under the rotation of an angle of $\alpha$ is measured again and several, 60 to 360 times of, similar operations are performed. Thereafter, data provided by these many projectional distributions of X-ray are calculated by Fourier transform or a convolution method, and a tomography of the X-ray tested tissue of body b is reproduced on the basis of a result of the processing.

However, in this type of a conventional X-ray computed tomography, it is necessary to have many projectional distributions of X-ray in order to reproduce a tomogram of an X-ray analyzed tissue b, resulting in some problems as follows:

(1) Since a long period of time is needed (several seconds to several minutes) for measuring, it is not possible to reproduce a tomogram of a moving tested tissue of body b.

(2) Exposure to X-ray is at a high level, resulting in some bad effects to the tested tissue of a body when the tested or analyzed tissue b is a living thing such as a human body.

The present invention is provided to overcome these disadvantages and its object is to provide a reconstruction method of X-ray computed tomography in which a reconstruction image having a high accuracy or precision may be produced by using only a projectional distribution of X-rays as data for reconstructing a tomogram of the tissue being analyzed.

SUMMARY OF THE INVENTION

In reference to the above description, the reconstruction method of X-ray computed tomography of the present invention is characterized in that each of a plurality of projectional distributions of X-ray produced by projecting X-rays from a plurality of desired directions toward the tissue of body being analyzed, each of the values at a plurality of positions properly spaced apart with each other in sequence from one end of each of the projectional distributions of X-rays to the other end thereof is measured, respectively, the measured values produced from one of a plurality of the projectional distributions of X-rays are designated the major data, the measured values produced from the remaining ones of a plurality of the projectional distributions of X-ray are designated as sub-data, and the X-ray absorption coefficient of the picture elements constituting a tomographic plane containing the tissue of body is calculated on the basis of the measured values produced from a plurality of the projectional distributions of X-rays, resulting in that a tomogram of said the tissue being analyzed by X-ray is reconstructed.

A reconstruction method of X-ray computed tomography of the present invention is characterized in that each of a plurality of projectional distributions of X-rays produced by projecting X-ray from a plurality of desired directions toward a tissue of a body is measured for its number N at a plurality of positions (N) properly spaced apart from each other from one end of one of the plurality of projectional distributions of X-rays to the other end thereof, each of the values at a plurality of proper positions properly spaced apart with each other from one end of the remaing one of the plurality of projectional distributions of X-rays to the other end thereof is measured, an absorption coefficient of X-rays for each of the picture elements constituted by the number N of picture elements and placed in a tomographic plane containing the X-ray tested tissue is calculated, and thereby a tomogram of the X-ray tested or analyzed tissue of body is reconstructed.

A reconstruction method of X-ray computed tomography of the present invention is characterized in that the X-ray absorption coefficient of each of the picture elements in a first group of picture elements constituted by the number u of the picture elements is calculated at first in reference to each of the measured values at a plurality of positions (u) properly spaced apart from each other in a sequence from one end of one of the a plurality of projectional distributions of X-rays produced by projecting X-rays from a plurality of desired directions toward an X-ray tested tissue of body to the other end thereof and further to each of the measured values at a plurality of proper positions properly spaced apart from each other in a sequence from one end of the remaining projectional distributions of X-rays of said plurality of projectional distributions of X-rays to the other end thereof, then the X-ray absorption coefficient of each of the picture elements in a second group of picture elements constituted by the number u of the picture elements is calculated in reference to each of the measured values at a plurality of positions (u) properly spaced apart with each other in a sequence from a measuring position of u+1 counted from one end of one of the plurality of projectional distributions of X-rays to the other end thereof, each of the measured values at a plurality of proper positions properly spaced apart with each other in a sequence from a proper measuring position counted from one end of the remaining projectional distributions of X-rays of the plurality of projectional distributions of X-rays to the other end thereof and the X-ray absorption coefficient of each of the picture elements in the first group of picture elements, and similarly in sequence the X-ray absorption coefficient of each of the picture elements in the subsequet group of picture elements constituted by the number u of picture elements is calculated, these groups of picture elements are arranged in their relative order, and thereby a tomogram of the X-ray tested tissue of body is reconstructed.

A reconstruction method of X-ray computed tomography of the present invention is characterized in that each of the values of the number M is measured at a plurality of positions (M) properly spaced apart with each other from one end of one of a plurality of projectional distributions of X-rays produced by projecting X-ray from a plurality of desired directions toward an X-ray tested tissue of body to the other end thereof, each of the values is measured at a plurality of proper positions properly spaced apart from each other from one end of the remaining projectional distributions of X-rays of said plurality of projectional distributions of X-rays to the other end thereof, respectively, the X-ray absorption coefficient of each of the picture elements constituted by the number of N of picture elements which is fewer then the number M and placed in a tomographic plane containing the X-ray analyzed tissue of a body is calculated in reference to these measured values, and thereby a tomogram of the X-ray tested tissue is reconstructed.

A reconstruction method of X-ray computed tomography of the present invention is characterized in that the X-ray absorption coefficient of each of the picture elements in a first group of picture elements constituted by the number u of picture elements fewer than the number of measured values $v_1$ produced from one of the plurality of projectional distributions of X-rays is calculated at first in reference to each of the measured values at a plurality of positions ($v_1$) properly spaced apart with each other from one end of one of a plurality of projectional distributions of X-rays produced by projecting X-rays from a plurality of desired directions toward the X-ray analyzed tissue to the other end thereof and each of the measured values at a plurality of proper positions properly spaced apart in a sequence from one end of the remaining projectional distributions of X-rays of the plurality of projectional distributions of X-rays, then the X-ray absorption coefficient of each of the picture elements in a second group of picture elements constituted by the number u of picture elements fewer than the number of the measured values $v_2$ produced by one of the plurality of projectional distributions of X-ray is calculated in reference to each of the measured values at a plurality of positions ($v_2$) properly spaced apart in a sequence from a proper measuring position from one end of one of said plurality of projectional distributions of X-rays toward the other end thereof, each of the measured values at a plurality of proper positions properly spaced apart from each other in sequence from a in proper measuring position at one end of the remaining ones of the plurality of projectional distributions of X-rays toward the other end thereof and the X-ray absorption coefficient of each of the picture elements in the first group of picture elements, similarly in a sequence the X-ray absorption coefficient of each of the picture elements in the subsequent groups picture elements constituted by the number of u of picture elements is calculated, these groups of picture elements are arranged in their relative orders and thereby a tomogram of said X-ray analyzed tissue is reconstructed.

Therefore, the following effects and advantages are provided by the reconstruction method of the X-ray computed tomography of the present invention.

(1) Since it is possible to reconstruct a tomogram of the X-ray tested tissue B in reference to a plurality of projectional distributions of X-rays made by projecting X-rays from a plurality of the specified directions from an extremely fewer number than that of conventional methods, a very short period of time is needed for sampling data as compared to that of conventional methods, and further a tomogram of the moving X-ray tested tissue B (e.g. heart) may clearly be produced with a high accuracy.

(2) Exposure to X-ray is at low value (several tenths to several hundredths compared with that of a conventional method), resulting in that bad effects might not result in to the tested tissue of a body when the tested tissue B is a living thing.

(3) Since it is possible to calculate the X-ray absorption coefficient of each of the picture elements for each of the groups of picture elements, a volume of data required for one processing may substantially be decreased and thereby a substantial simplified data processing may be performed as well as a cost reduction for the data processing device may sufficiently be accomplished.

(4) Since a X-ray computed tomography may be reproduced on the basis of data more than the number u of picture elements constituting a group of picture elements formed as a partial plane of the surface of tomography S including an X-ray tested tissue, of a body, B, it is possible to provide a highly improved accuracy in a reconstruction of the tomogram.

BRIEF DESCRIPTION OF THE DRAWINGS

In reference to the drawings, preferred embodiments of the present invention will be described below.

FIGS. 2 to 4 illustrate a reconstruction method of X-ray computed tomography of a first preferred embodiment of the present invention wherein, FIG. 2 is a schematic illustration for showing means for measuring a projectional distribution of X-rays.

FIG. 3 is a diagram for showing an arrangement of the system.

FIG. 4 is a schematic illustration for showing operation of the system.

DESCRIPTION OF THE PREFERRED EMBODIMENTS OF THE INVENTION

Figure 1:
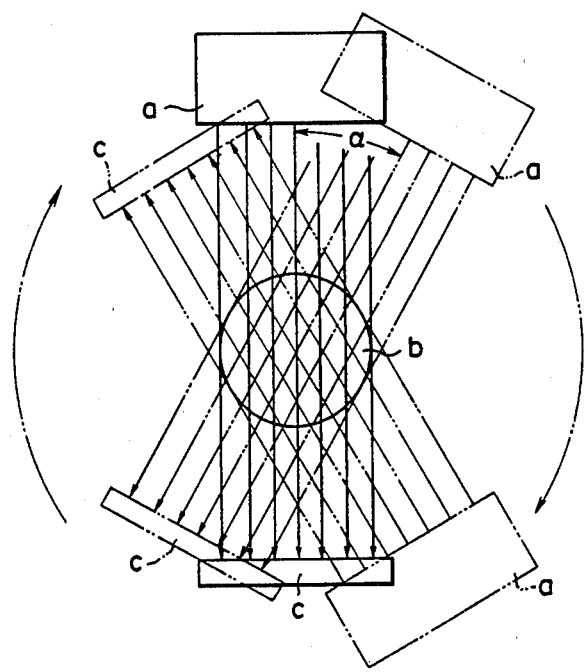
FIG. 1 is a schematic illustration showing the operation of a conventional tomographic system.
Figure 2:
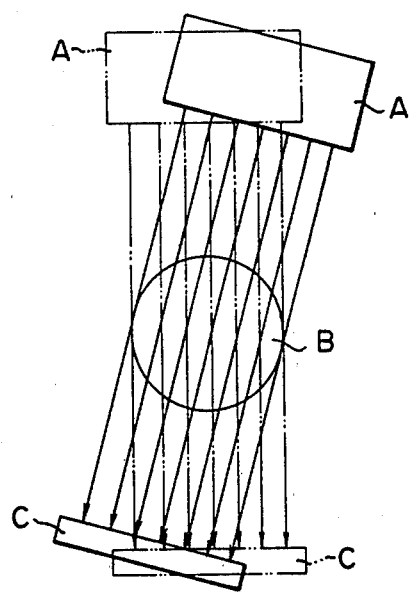
Figure 3:
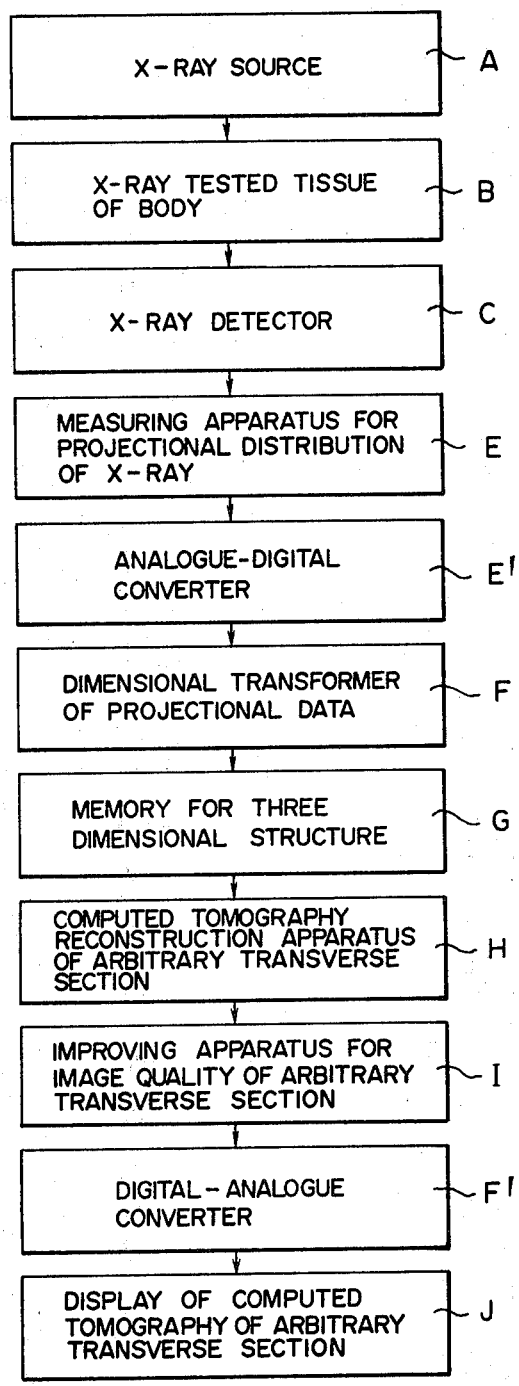
Figure 4:
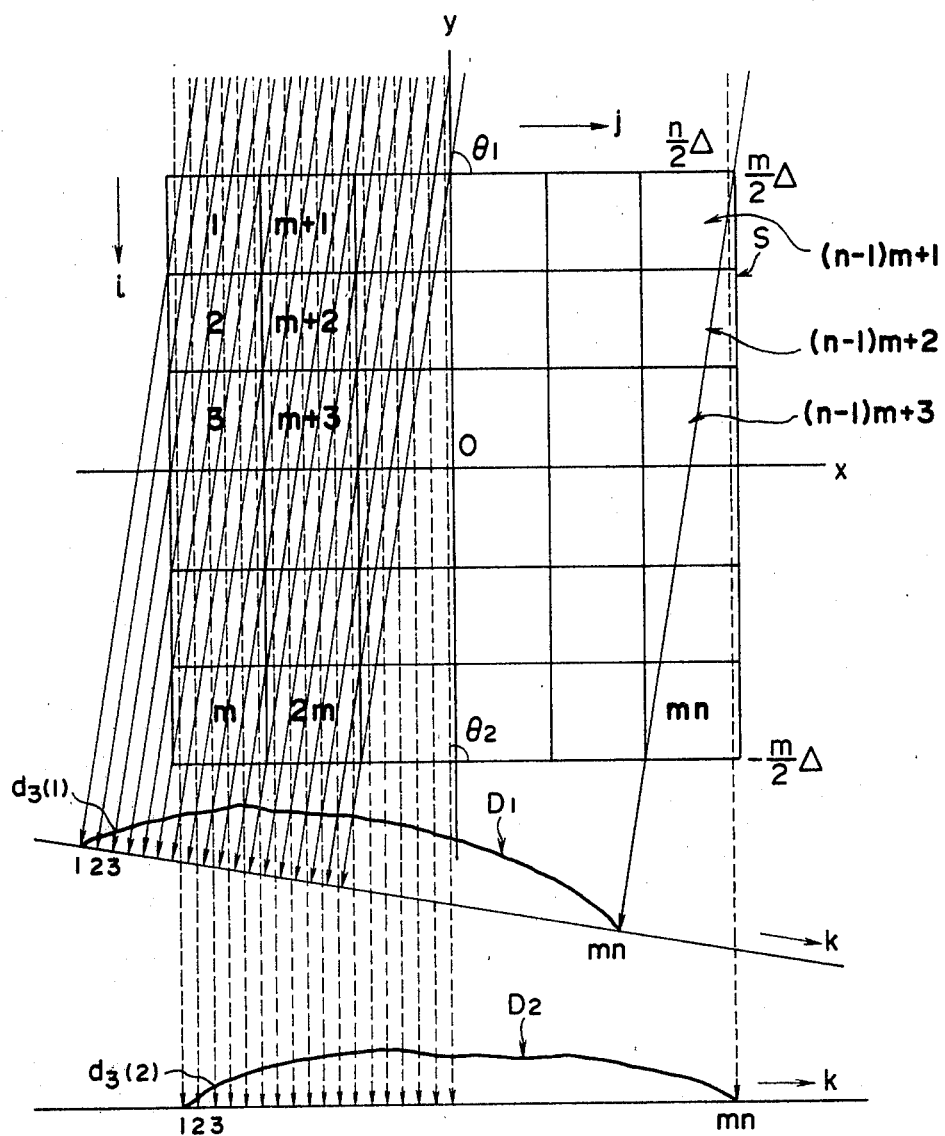

In the first preferred embodiment of the present invention illustrated in FIGS. 2 to 4, an X-ray tested, tissue of a body, B is to be positioned between an X-ray source A and an X-rays detector C, and thereby X-ray may be projected from a plurality of desired directions (2) the X-ray tested tissue B, resulting in that the first and second projectional distributions of X-rays $D_1$ and $D_2$ (see FIG. 4) may be produced by X-rays passed through X-ray tested tissue B.

The X-ray source A is a device capable of producing X-rays having a quality (a transmittance power) and a dose which are suitable for X-ray tested, tissue of a body, B forming an object to be inspected or analyzed. The X-ray source A is provided with a driving mechanism for enabling the source to be rotated, by a specified angle, around the X-ray tested tissue B.

The wave length of the produced X-ray is proportional to the voltage applied, and a dose of X-ray is determined in reference to the wave length of the X-ray, the applied voltage is varied in accordance with the actual application, such, a as range of 50,000 to 120,000 volts for a medical diagnosis and a range of 100,000 to 300,000 volts for non-destructive testing.

The X-ray tested tissue B is one which is to be radiated by X-ray and its distribution of transmitted dose (projectional distribution of X-ray) is measured and thereby the image at a desired plane of tomography is to be reconstructed. For example, in a medical diagnosis the tissue is part of a human body (in general a living thing) and in turn in case of a non-destructive test, it is an industrial product.

Further, as an X-ray detector C, there are used such as a X-ray film, a scintillation detector, a semi-conductor sensor or a xeon gas sensor etc., and X-ray detector C is also provided with a driving mechanism for enabling the detector to be rotated around the X-ray tested tissue of body B by a desired corresponding angle.

Then, the first data $D_1$ of a projectional distribution of X-rays is detected as major data by X-ray detector C are constructed such that each of the values $d_k(1)$ at the positions of the number of mn (=N) equally spaced apart from each other by a distance w is calculated by a measuring apparatus for projectional distribution of X-ray E from one end of the first projectional distribution of X-ray $D_1$ to the other end thereof, and in turn the second data $D_2$ of projectional distribution of X-rays produced as sub-data by X-ray detector C upon moving the X-ray source A and X-ray detector C from the condition above are constructed such that each of the values $d_k(2)$ at the positions of the number of mn equally spaced apart from each other by a distance w is calculated similarly by a measuring apparatus for projectional distribution of X-ray E from one end of said second projectional distribution of X-ray $D_2$ to the other end thereof (see FIG. 4).

As the measuring apparatus for projectional distribution of X-ray E, when X-ray detector C is an X-ray film, a micro-densitometer is used capable of measuring a plurality of values on a distribution of the density of X-rays (so-called roentgenograph) which is obtained on X-ray film as a dark or light pattern of darkness. In the present invention, it is necessary to apply two X-ray films in response to the actual requirement of two types of distribution of the density of X-rays.

In this way, as means for measuring each of the values $d_k(1)$ and $d_k(2)$ at a plurality of positions equally spaced apart by a distance w with each other starting from one end of the first and second projectional distributions of X-rays $D_1$ and $D_2$ to the other end thereof, a scintillation detector is used in addition to the examples described above for producing a signal corresponding to the density of X-ray in which the X-ray detector C receives X-ray transmitted through the X-ray tested tissue B, and in this case, one unit of a scintillation detector and a mechanism for moving the detector from one end of the first and second projectional distributions of X-ray $D_1$ and $D_2$ to the other end thereof are combined with each other or a number of scintillation detectors are arranged over the entire width of the projectional distribution of X-rays.

Also in case that the X-ray detector C is made of a semi-conductor type detector which will produce a signal corresponding to the density of the X-ray after receiving the X-ray transmitted through the tissue B, one semi-conductor detector and a mechanism for moving the detector are combined with each other or a number of semiconductor detectors are arranged in the same manner as in the case in which the scintillation detector described above is applied as said means.

In case that the X-ray detector C is made as a xenon gas detector, one xeon gas detector and a mechanism for moving the detector are combined with each other or a number of xeon gas detectors are arranged in the same manner as that the above described scintillation detector or a semiconductor detector as said means.

In turn, in case that the X-ray detector C is made of a one scintillator detector, one semi-conductor detector or a combined unit of one xeon gas detector and a moving drive mechanism, each of the detectors is usually scanned two times, and to the contrary in case that a number of scintillator detectors, semi-conductor detectors or a number of xenon gas detectors are arranged, the measurement operation is performed by these many detectors.

The signal produced by the measuring apparatus for projectional distribution of X-ray in this way is an analogue signal, this signal is transformed to a digital signal by an analogue-digital converter E' (hereinafter called "A/D converter") in order to apply the signal to a digital computer, and then the signal is stored in a disk etc.

Thereby, a first means is constituted by which a plurality (N) of the values $d_k(1)$ on the first projectional distribution of X-ray $D_1$ and a plurality (mn) of the values $d_k(2)$ on the second projectional distribution of X-rays $D_2$ produced by projecting X-ray from desired two directions toward an X-ray tested tissue B may be measured, respectively, by the measuring apparatus for projectional distribution of X-rays E or A/D converter E' etc.

Then, the data outputs $d_k(1)$ and $d_k(2)$ (digital signal) produced from the first means are fed to a dimensional transformer of projectional data F constituting a second means, respectively.

This dimensional transformer of projectional data F may produce upon calculation a signal corresponding to each of the X-ray absorption coefficients (two dimensional data) of the number mn (=N) of picture elements constituting a pseudo-tomographic plane S containing a plane of tomography of an X-ray tested tissue B on the basis of the number of the number mn (=N) of the first digital data output $d_k(1)$ (one dimensional data) and the number mn of the second digital data output $d_k(2)$ of a second projectional distribution of X-ray (one dimensional data) produced from the first means, respectively.

As a practical embodiment, a digital computer storing a desired program may be used.

Then, a calculation method will be described as follows in which each of the X-ray absorption coefficients $\mu_1$ to $\mu_{mn}$ (two dimensional data) of the number of mn of picture elements as a constituting component of the pseudo-tomographic plane S containing a tomographic plane of X-ray tested tissue B is calculated in reference to the number of mn (=N) the measured value $d_k(1)$ (one dimensional data; major data) on the first projectional distribution of X-rays $D_1$ produced by the first means and similarly the number of mn of the measured value $d_k(2)$ (one dimensional data; sub-data) on the second projectional distribution of X-rays $D_2$ produced by the first means.

At first, assuming that a pseudo-tomographic plane S applied as a reconstruction plane of tomography for the X-ray tested tissue B is, as shown in FIG. 4, is constituted by the number of mn (=N) of the divided small picture elements, and further a center of the plane S is positioned at an origin of the x-y coordinates.

Further, it is assumed that the numbers m and n are even numbers, and a size of one picture element is a square of $\Delta \times \Delta$ for a convenience of description.

Further, it is assumed that X-ray beams passing through the pseudo-tomographic plane S are projected in parallel from two different directions having a relation of $\theta_1 = \tan^{-1} m$ and $\theta_2 = \pi/2$, and a diameter of each of the unit X-ray beams is sufficiently small compared with that of each of the picture elements.

If it is assumed that each of the picture elements is provided with a number in accordance with the order as shown in FIG. 4, the absorption coefficient is defined by $\mu_k$, each X-ray beam is projected or transmitted from a direction of $\theta_1$, a projection density made by the first unit of X-ray beam passing through a point $(x_j, y_i)$ in x-y coordinates is defined as $d_k(1)$ and the following equation may be provided.

$$x_j = \left(-\frac{n}{2} + j - 1\right) \cdot \Delta$$

$$y_i = \left(\frac{m}{2} - i\right) \cdot \Delta$$

$$k = (j-1) \cdot m + i$$

($i = 1, 2, \ldots m$; $j = 1, 2, \ldots n$), where, i is a row and j is a column.

And further if it is assumed that the projectional density produced by the second of X-ray beam in a direction from $\theta_2$ is expressed by $d_k(2)$, the following equation may be provided.

And it is assumed that the X-ray beams projected from a direction $\theta_2$ are radiated equally spaced apart with a space or a distance $w = \Delta/m$ $$\mathbb{L} \, \mu = \mathbb{D} \qquad \qquad (1)$$

where, $$\mathbb{L} = \begin{pmatrix} \text{matrix as shown} \end{pmatrix} \qquad (2)$$

and where, $$\mu = (\mu_1, \mu_2, \mu_3, \ldots, \mu_{mn})^T$$

$$\mathbb{D} = (d_1(1)/\alpha, d_2(1)/\alpha, \ldots, d_{mn}(1)/\alpha, d_1(2), d_2(2), \ldots, d_{mn}(2))^T$$

and is a matrix of $2\ mn \times mn$.

A value of $\alpha$ is a length of the X-ray beams passing through one picture element from a direction of $\theta_1$, and fulfills an equation of $$\alpha = \Delta \cdot \sqrt{1 + \cot^2 \theta_1}$$

and the symbol T represents a transpose.

As described above, it is assumed that an equation of $mn = N$ is fulfilled.

Resolving the equation (1) by applying a method of least squares shows two dimensional tomographic data $\mu_1$ to $\mu_N$ of the X-ray tested tissue B. However, the data in general have some measuring errors.

Thus, in order to apply a mathematical programming, non-negative correction values of $r_1, r_2, r_3 \ldots, r_{2N}$ are applied.

Since an absorption coefficient of an X-ray beam passing through an object is generally a non-negative value and does not exceed a positive upper limit value U which may be defined physically, the equation (1) will be expressed as follows by applying these constraints.

$$\left. \begin{array}{l} l_{1\cdot1}\mu_1 + l_{1\cdot2}\mu_2 + \ldots + l_{1\cdot N}\mu_N - r_1 \leq p_1 \\ l_{1\cdot1}\mu_1 + l_{1\cdot2}\mu_2 + \ldots + l_{1\cdot N}\mu_N + r_1 \geq p_1 \\ l_{2\cdot1}\mu_1 + l_{2\cdot2}\mu_2 + \ldots + l_{2\cdot N}\mu_N - r_2 \leq p_2 \\ l_{2\cdot1}\mu_1 + l_{2\cdot2}\mu_2 + \ldots + l_{2\cdot N}\mu_N + r_2 \geq p_2 \\ \ldots \\ \ldots \\ l_{2N\cdot1}\mu_1 + l_{2N\cdot2}\mu_2 + \ldots + l_{2N\cdot N}\mu_N - r_{2N} \leq p_{2N} \\ l_{2N\cdot1}\mu_1 + l_{2N\cdot2}\mu_2 + \ldots + l_{2N\cdot N}\mu_N + r_{2N} \geq p_{2N} \\ \mu_1 \leq U, \mu_2 \leq U, \ldots, \mu_N \leq U \\ \mu_1 \geq O, \mu_2 \geq O, \ldots, \mu_N \geq O \\ r_1 \geq O, r_2 \geq O, \ldots, r_{2N} \geq O \end{array} \right\} \quad (3)$$

where, $p_1 = d_1(1)/\alpha, p_2 = d_2(1)/\alpha, \ldots, p_N = d_N(1)/\alpha,$ $p_{N+1} = d_1(2), p_{N+2} = d_2(2), \ldots, p_{2N} = d_N(2)$ Solution having the minimum value of the object function of $$F = \sum_{k=1}^{2N} r_k \quad (4)$$

is calculated by a mathematical programming under an equation (3) of restrictive condition, resulting in showing the most suitable two dimensional data $\mu_1$ to $\mu_N$ after the calculation of limited times.

In the above example, the two dimensional data for a tomography have been calculated under an object function for making the minimum sum of an absolute value of the correction in the equation of restrictive condition, there is also another method in which the object function of the equation (6) is made to be the minimum one under the equation of restrictive condition of the following equation (5).

$$\left. \begin{array}{l} l_{1\cdot1}\mu_1 + l_{1\cdot2}\mu_2 + \ldots + l_{1\cdot N}\mu_N - r \leq p_1 \\ l_{1\cdot1}\mu_1 + l_{1\cdot2}\mu_2 + \ldots + l_{1\cdot N}\mu_N + r \geq p_1 \\ l_{2\cdot1}\mu_1 + l_{2\cdot2}\mu_2 + \ldots + l_{2\cdot N}\mu_N - r \leq p_2 \\ l_{2\cdot1}\mu_1 + l_{2\cdot2}\mu_2 + \ldots + l_{2\cdot N}\mu_N + r \geq p_2 \\ \ldots \\ \ldots \\ l_{2N\cdot1}\mu_1 + l_{2N\cdot2}\mu_2 + \ldots + l_{2N\cdot N}\mu_N - r \leq p_{2N} \\ l_{2N\cdot1}\mu_1 + l_{2N\cdot2}\mu_2 + \ldots + l_{2N\cdot N}\mu_N + r \geq p_{2N} \\ \mu_1 \leq U, \mu_2 \leq U, \ldots, \mu_N \leq U \\ \mu_1 \geq O, \mu_2 \geq O, \ldots, \mu_N \geq O, r \geq O \end{array} \right\} \quad (5)$$

$$F = r \quad (6)$$

Upon solving the above equation, the tomographic two dimensional data $\mu_1$ to $\mu_N$ of the X-ray tested tissue B is calculated under such conditions as the maximum corrected value of the absolute value under the equation of the restrictive condition is made to be minimum.

Further, the calculation may also be made by a method in which an object function of $$F = \sum_{k=1}^{2N} r_k^2 \quad (7)$$

is made to be minimum under the equation of the restrictive condition of the equation (3), or a method in which an object function of $$F = r^2 \quad (8)$$

is made to be minimum under an equation of the restrictive condition of the equation (5).

The two dimensional data $\mu_1$ to $\mu_N$ made in this way are transmitted to the memory for three dimensional structure G shown in FIG. 3, respectively.

This memory for three dimensional structure G is such a memory as the two dimensional data $\mu_1$ to $\mu_N$ for use in making the tomogram transmitted from the dimensional transformer of projectional data F are stored in a time sequence and the data of the three dimensional structure of the X-ray tested tissue B are calculated.

Thus, the two dimensional data $\mu_1$ to $\mu_N$ transmitted at first from the dimensional transformer of projectional data F are related to a certain transverse section of X-ray tested tissue B, other projectional distributions of X-rays $D_1'$, $D_2'$ may be made by changing a measuring point with the measuring apparatus for projectional distribution of X-rays E, and the two dimensional data $\mu_1'$ to $\mu_N'$ relating to other sections may easily be obtained, and so it will become possible to store the inner three dimensional structure of X-ray tested tissue B by accumulating two dimensional data $\mu_1$ to $\mu_N$, $\mu_1'$ to $\mu_N'$, $\mu_1''$ to $\mu_N''$, . . . relating to some different sections. However, in order to make a complete three dimensional structure, an interpolation etc. between each of the section data will be required, so that the present memory G may be applied as a memory device holding a calculation function.

To this memory G is connected a computed tomography reconstruction apparatus of arbitrary transverse section H. This computed tomography reconstruction apparatus of arbitrary transverse section H is such a device as the two dimensional data relating to the specified arbitrary transverse section of the X-ray tested tissue B are selectively retrieved from the data of three dimensional inner structure of X-ray tested tissue B stored in the memory G and thereby a tomogram is reconstructed.

In this paragraph, the term of arbitrary transverse is defined as a section which is horizontal, vertical or inclined to the X-ray tested tissue B.

The two dimensional data relating to the arbitrary tomography made in this way by the computed tomography reconstruction apparatus of arbitrary transverse section H are mathematically and correctly calculated in response to the projectional distribution of X-rays produced by the measuring apparatus for projectional distribution of X-rays E, so that if the data are transmitted to and displayed on a display of computed tomography of arbitrary transverse section J for displaying data via suitable digital-analogue converter F' (hereinafter called "D/A converter"), it is possible to display a tomogram of an X-ray tested tissue B. However, this tomography has such bad inferior components as noise or a vague picture, so that no guarantee is made for getting a proper picture image.

Therefore, in order to correct data obtained from the computed tomography reconstruction apparatus of arbitrary transverse section H, the data are fed or transmitted to an improving apparatus for image quality of arbitrary transverse section I.

This improving apparatus for image quality of arbitrary transverse section I is made such that an image quality is improved by removing some noises, making a smoothness and a sharpness of the data of tomography of arbitrary transverse section transmitted from the computed tomography reconstruction apparatus of arbitrary transverse section H. A digital filter is used for eliminating the noise, a smoothing circuit is used for smoothing operation, and a differentiation circuit is used for amplifying a sharpness of the image.

The signal of which image quality has been improved is transmitted to the display of computed tomography of arbitrary transverse section J via D/A converter F'.

The display of computed tomography of arbitrary transverse section J is such a device as it receives a signal transmitted from the improving apparatus for image quality of arbitrary transverse section I and displays the arbitrary tomography of X-ray tested tissue B as a visible image upon a monitor of a color or monochromatic cathode-ray tube (Braun tube), and in general the Braun tube is used as described above.

In order to reconstruct a tomogram of X-ray tested tissue B by an arrangement described above, the first one-dimensional data $d_k(1)$ (major data) are calculated at first by measuring each of the values at the number of N of positions equally spaced apart with each other by a distance w from one end of the first projectional distributions of X-rays $D_1$ produced by X-ray detector C by projecting X-ray in a desired direction $\theta_1$ from the X-ray source A toward the X-ray tested tissue B to the other end of said first projectional distributions of X-rays $D_1$, and second one dimensional data (sub-data) $d_k(2)$ are calculated by measuring each of the values $d_k(2)$ at the number of N of positions equally spaced apart with each other by a distance w from one end of the second projectional distributions of X-rays $D_2$ produced by the X-ray detector C by projecting X-ray in another specified direction $\theta_2$ toward the X-ray tested tissue of body B from the X-ray source A with the measuring means for projectional distribution of X-ray E.

Then, these number of 2 N of one-dimensional data $d_k(1)$ and $d_k(2)$ are properly converted from their analogue form to digital one, and thereby the number of N of the X-ray absorption coefficients $\mu_1$ to $\mu_N$ are calculated by the above-mentioned method at the dimensional transformer of projectional data F.

Then, these two dimensional data $\mu_1$ to $\mu_N$ are reconstructed and displayed as the tomography of the X-ray tested tissue of body B by the display of computed tomography of arbitrary transverse section J through the memory G, the computed tomography reconstruction apparatus of arbitrary transverse section H, the improving apparatus for image quality of arbitrary transverse section I and D/A converter F'.

Figure 5:
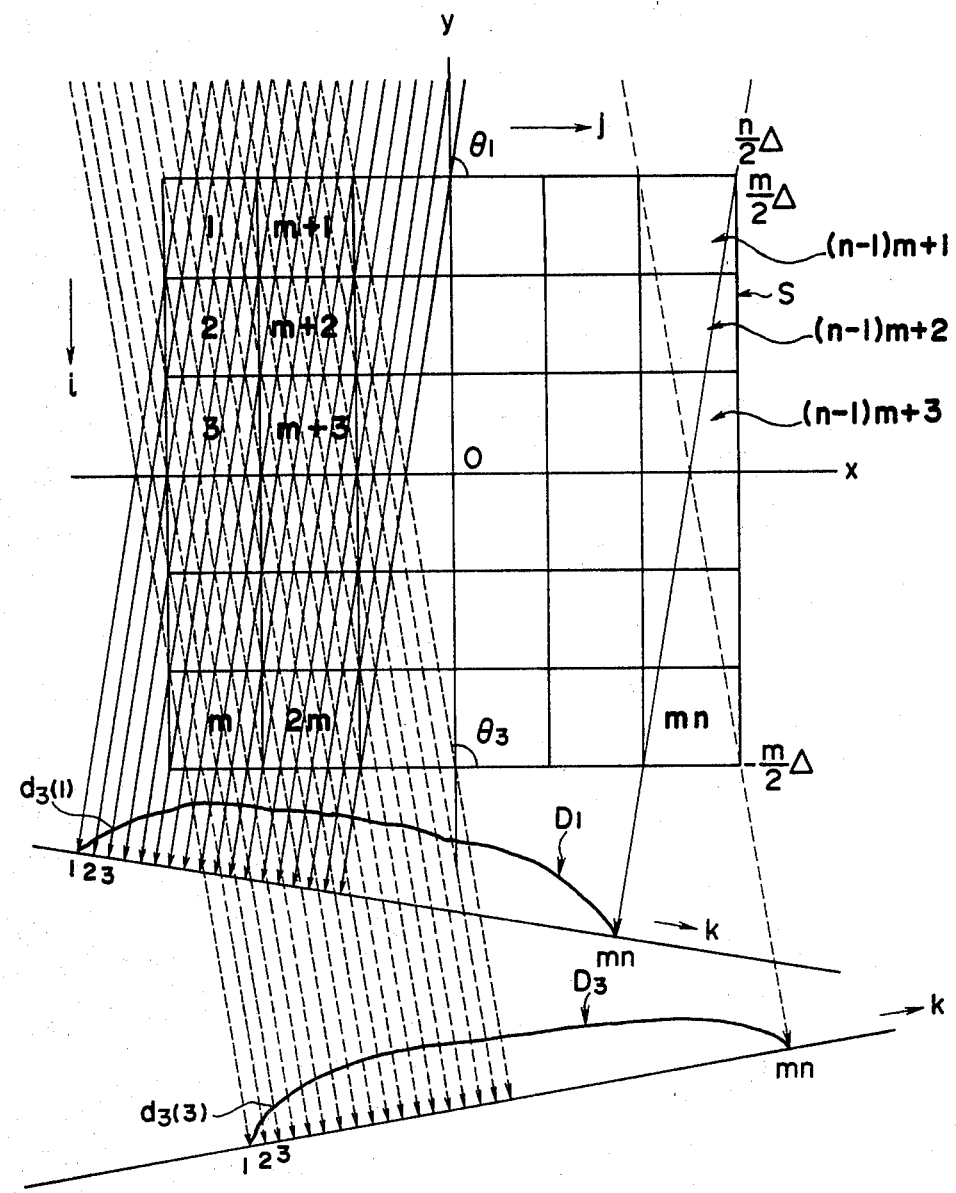
FIG. 5 is a schematic illustration for indicating an operation of the reconstruction method of X-ray computed tomography in a second preferred embodiment of the present invention.

FIG. 5 is a schematic view for illustrating a reconstruction method for X-ray computed tomography of a second preferred embodiment of the present invention wherein the similar numbers in FIG. 5 substantially correspond to that of FIGS. 2 to 4.

Also in the second preferred embodiment of the present invention, it is assumed that the pseudo-tomographic plane S of a reconstructional plane of the tomography of X-ray tested tissue B is constituted by the number of mn of the divided small picture elements 1 to mn, as shown in FIG. 5, and a center of the plane S is placed at an origin of x-y coordinates and further it is assumed that the numbers m and n are even number, and a size of one picture element is a square of $\Delta \times \Delta$ for a convenience of description.

Further, it is assumed that X-ray beams passing through the pseudo-tomographic plane S are projected in parallel by the number of mn (=N) from two directions fulfilling a relation of $\theta_1 = \tan^{-1} m$ and $\theta_3 = -\tan^{-1} m$ as different from that of the above mentioned preferred embodiment.

Further, it is assumed that a diameter of each of the unit X-ray beam is sufficiently small compared with that of each of the picture elements.

In this way, if it is assumed that the specified two directions for projecting X-ray beam are $\theta_3$ and $\theta_4$, respectively, the foregoing equation (1) may be expressed as follows.

$$L \cdot \mu = D' \qquad (8)$$

where

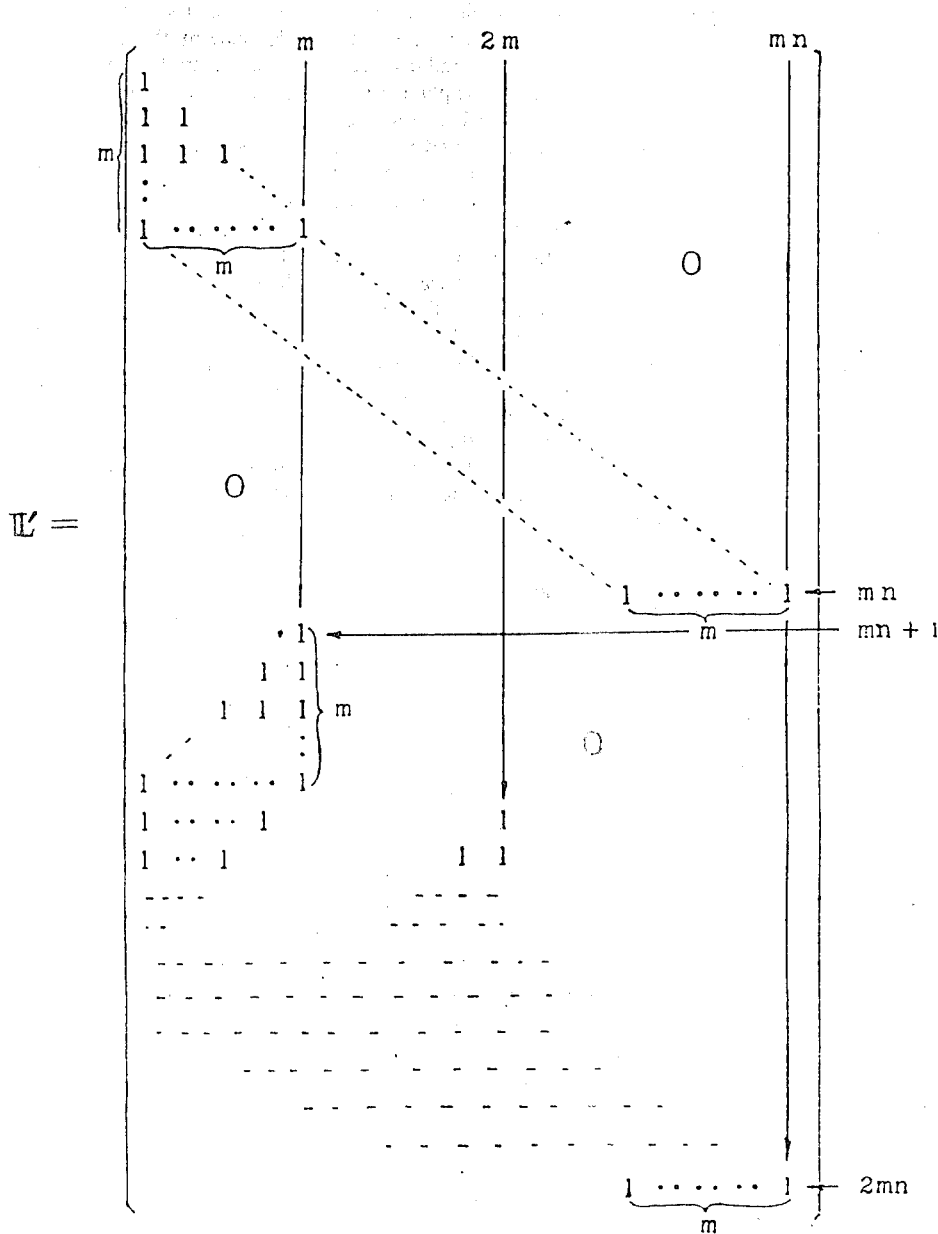

$$\dots\dots\dots\dots \quad (9)$$

$$\mathbb{P} = (\mu_1, \mu_2, \mu_3, \dots, \mu_{mn})^T$$

$$\mathbb{D}' = (d_1(1), d_2(1), \dots, d_{mn}(1), d_1(3), d_2(3), \dots, d_{mn}(3))^T/\alpha$$

And $d_k(1)$ and $d_k(3)$ show the measured value produced by projecting X-ray beam from the directions $\theta_1$ and $\theta_3$.

A value of $\alpha$ is a length of X-ray beams passing through one picture element in the directions $\theta_1$ and $\theta_3$ and fulfills a relation $$\alpha = \Delta \cdot \sqrt{1 + \cot^2 \theta_1} = \Delta \cdot \sqrt{1 + \cot^2 \theta_3}$$

and a symbol T represents a transposition.

Resolving the equation (8) under the method of least squares may enable a calculation of the two dimensional data $\mu_1$ to $\mu_{mn}$ of a tomogram of the X-ray tested tissue B substantially in the same manner as that of the above mentioned preferred embodiment. However, in general, the data contain some measuring errors, so that the measuring errors are made a minimum by a mathematical programming substantially in the same manner as that of the above mentioned preferred embodiment.

Then, the signals corresponding to the X-ray absorption coefficients $\mu_k$ as the two dimensional data obtained in this way are transmitted to the memory G, reconstructed and displayed as the tomography of the X-ray tested tissue B by the display of computed tomography of arbitrary transverse section J through the computed tomography reconstruction apparatus of arbitrary transverse section H, the improving apparatus for image quality of arbitrary transverse section I and D/A converter F'.

Further, in addition to the above described first and second preferred embodiments, it is possible to apply such values as $\tan^{-1} m$, $0$ or $\tan^{-1} m$, $\pi/2 \pm \tan^{-1} m$ etc. as an example of two projectional directions. Also in this case, as substantially in the same manner as that of each of the preferred embodiments, the number mn ($=N$) of the X-ray absorption coefficients may be calculated and a tomogram of the X-ray tested tissue of a body may be reconstructed.

Figure 6:
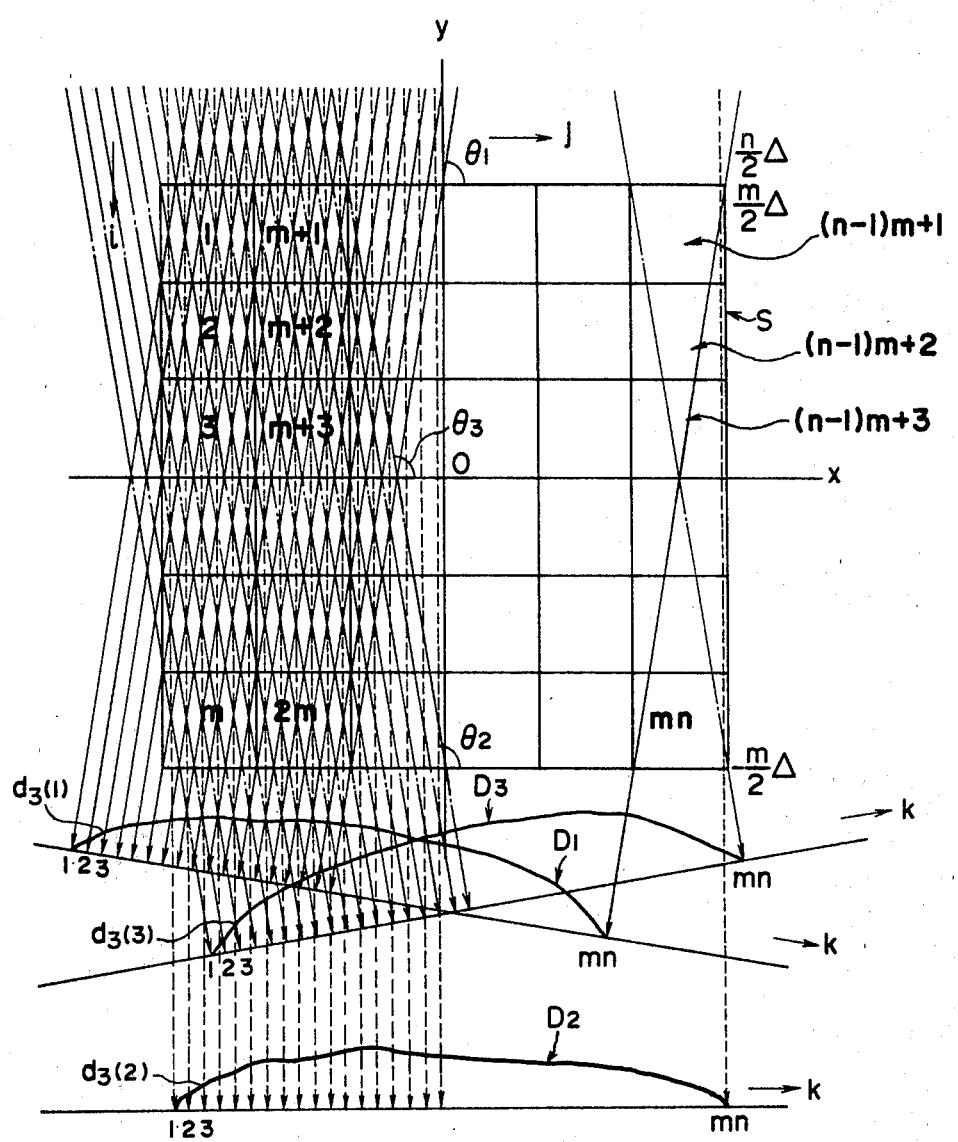
FIG. 6 is a schematic illustration for indicating operation of the reconstruction method of X-ray computed tomography in a third preferred embodiment of the present invention.

FIG. 6 is a schematic illustration for showing a reconstruction method of an X-ray computed tomogram as a third preferred embodiment of the present invention, the similar reference characters used in FIGS. 2 to 5 show substantially the same components.

Also in case of this third preferred embodiment, it is assumed that a pseudo-tomographic plane S applied as a tomographic reconstruction plane for the X-ray tested tissue B is, as shown in FIG. 6, made by the number of mn of the small divided picture elements 1 to mn, and a center of the plane S is placed at an origin of x-y coordinates. Further, for a convenience of description, the numbers m and n are even numbers and a size of one picture element is a square of $\Delta \times \Delta$.

Further, it is assumed that X-ray beams passing through the pseudo-tomographic plane S are, different from that of each of the preferred embodiments, projected in parallel from three directions fulfilling $\theta_1 = \tan^{-1} m$, $\theta_2 = \pi/2$ and $\theta_3 = -\tan^{-1} m$ by the number mn ($=N$).

And a diameter of each of the unit X-ray beams is sufficiently small compared with that of each of the picture elements.

Setting the desired three directions of X-ray projection to such conditions as $\theta_1$, $\theta_2$ and $\theta_3$ results in making the above mentioned equation (1) as follows.

$$L'' \, \mu = D'' \qquad (10)$$

where,

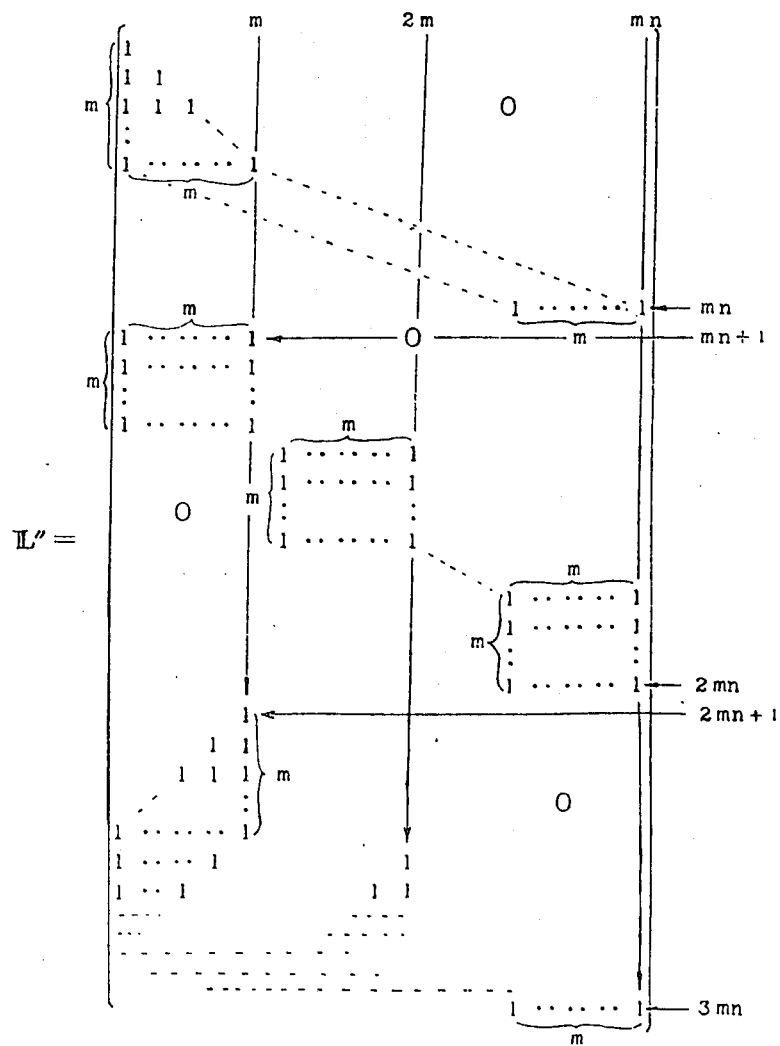

(11)

$$a = (\mu_1, \mu_2, \mu_3, \ldots, \mu_{mn})^T$$

$$\mathbb{D}'' = (d_1(1)/\alpha, d_2(1)/\alpha, \ldots, d_{mn}(1)/\alpha, d_1(2), d_2(2), \ldots, d_{mn}(2),$$

$$d_1(3)/\alpha, d_2(3)/\alpha, \ldots, d_{mn}(3)/\alpha)^T$$

The values of $d_k(1)$, $d_k(2)$ and $d_k(3)$ show the measured values produced by projecting X-ray beams from the directions of $\theta_1$, $\theta_2$ and $\theta_3$, respectively.

Resolving the equation (10) by applying a method of least square etc. may enable a calculation of the two dimensional tomographic data $\mu_1$ to $\mu_{mn}$ of the X-ray tested tissue B substantially in the same manner as that of each of said preferred embodiments. However, in general, the data above have some measuring errors, so that some errors produced in case of reconstruction by applying a mathematical programming substantially in the same manner as that of each of the preferred embodiments.

The signal corresponding to the X-ray absorption coefficients $\mu_k$ of the two dimensional data thus obtained are transmitted to the memory G, thereafter reconstructed and displayed as a tomography of the X-ray tested tissue of body B by the display of computed tomography of arbitrary transverse section J via computed tomography reconstruction apparatus of arbitrary transverse section H, the improving apparatus for image quality of arbitrary transverse section I and D/A converter F'.

Further, in addition to the above mentioned third preferred embodiment, it is possible to apply such values as $\tan^{-1} m$, $-\tan^{-1} m$, 0 or $\tan^{-1} m$, $\pi/2$ and 0 etc. as an example of three projectional directions, and also in this case, substantially in the same manner as that of each of the preferred embodiments, it is possible to calculate the number of mn (=N) of the X-ray absorption coefficients to reconstruct a tomogram of the X-ray tested tissue of a body.

And further, even if the projecting directions show more than three, it is possible to reconstruct the X-ray computed tomography in the same manner as above. On the contrary, an increased number of the projecting or emission directions may enable improving accuracy of measurement or reconstruction as well as to increase the time required for data processing and to make large-sized hardware, so that it is preferable to determine the number of projectional directions in reference to the above mentioned items.

Further, as in the same manner as that of each of the preferred embodiments, it is possible to measure the number N of each of one dimensional data from the one projectional distribution of X-ray and a proper number of (more than or less than the number N) each of one dimensional data instead of such an operation as the number of N of one dimensional data are measured from one of a plurality of the projectional distributions of X-ray and also the number N of one dimensional data are measured from the remaining projectional distributions of X-ray, and thereby to calculate the X-ray absorption coefficient of the two dimensional data in reference to these one dimensional data.

In case of the projecting beam of which the projecting direction is at a value of $\pi/2$ or 0, each of the partial planes of a column of the pseudo-tomographic plane S or each of the partial planes of a row thereof may be represented by a mean value of the number m or n of the beams and another value multiplied by the number m or n is added to the object function during its calculation process. In the later case, it is possible to save capacity of memory or to shorten the time of calculation.

Figure 7:
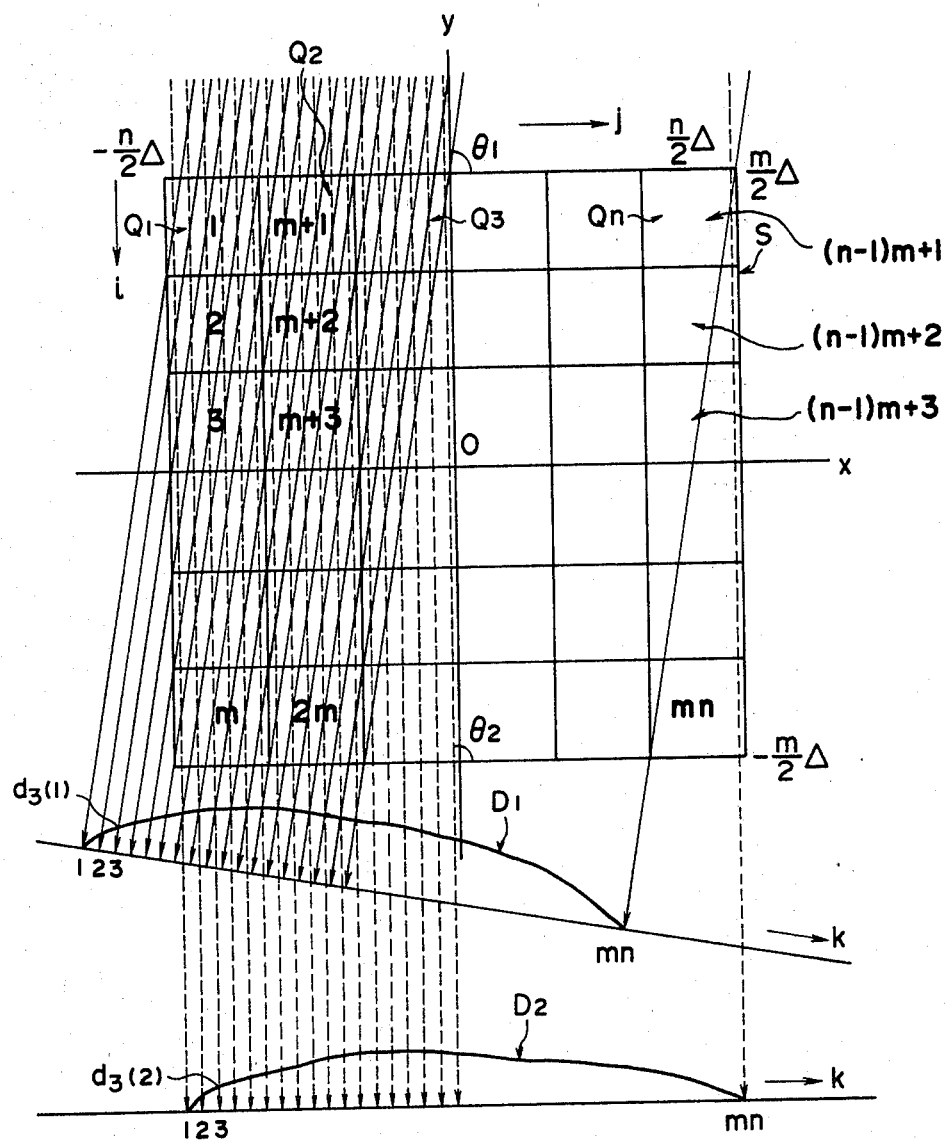
FIG. 7 is a schematic illustration for showing a reconstruction method of X-ray computed tomography in a fourth preferred embodiment of the present invention.

FIG. 7 is a schematic view for illustrating a reconstruction method of X-ray computed tomography of a fourth preferred embodiment of the present invention wherein the similar reference numbers in FIGS. 2 to 6 substantially correspond to that of this embodiment.

In the fourth preferred embodiment of the present invention, a set of n of the groups of the measured values constituted by the measured values applied as major data may be produced at a plurality of positions [u (=m)] properly spaced apart from each other in sequence from one end of the first projectional distribution of X-rays $D_1$ to the other end thereof and a set of n of (the number of 2mn in total) the groups of the measured values constituted by the measured values applied as sub-data may be produced at a plurality of positions (m) properly spaced apart with respect to each other in sequence from one end of the second projectional distribution of X-rays $D_2$ to the other end thereof, respectively, by the first means constituted by the means for measuring the projectional distribution of X-rays E and A/D converter E' etc. in reference to said first and second projectional distributions of X-rays $D_1$ and $D_2$ produced by projecting X-ray from a plurality of desired (two) directions toward the X-ray tested tissue B, and further the data outputs (digital signals) from the first means for each of the groups of measured values are fed in sequence to the dimensional transformer of projectional data F constituting the second means, respectively.

This dimensional transformer of projectional data F may calculate and feed in sequence by the number m of the signals corresponding to each of the X-ray absorption coefficients (two dimensional data) of each of the picture elements in a set n of the groups of picture elements constituted by the number u (=m) of picture elements, respectively, in reference to the data outputs for each of the groups of the measured values produced from the first means, that is, the data outputs of the first projectional distribution of X-rays (one-dimensional data; major data) and the data outputs of the second projectional distribution of X-rays (one-dimensional data; sub-data) corresponding to the data outputs of the first projectional distribution of X-rays, and as its practical or actual example, a digital computer storing some desired programs may be applied.

It will be described as follows a method in which each of the X-ray absorption coefficients (two-dimensional data) of the number mn of the picture elements constituting a pseudo-tomographic plane S (this plane S being composed of a set of n of the groups of picture elements) containing a tomography of the X-ray tested tissue B is calculated in reference to each of the groups of the measured values constituted by the number m of the measured values $d_k(1)$ (one-dimensional data) on the first projectional distribution of X-rays $D_1$ produced by the first means and also to each of the groups of the measured values constituted by the number of m of the measured values $d_k(2)$ (one-dimensional data) on the second projectional distribution of X-rays $D_2$ produced similarly by the first means.

At first, it is assumed that the pseudo-tomographic plane S applied as a tomography reconstruction plane of the X-ray tested tissue B is constituted by a set of n of the groups of picture elements applied as the partial plane of column of the tomography reconstruction plane composed of the number m of the picture elements divided into some small sections as shown in FIG. 7 and a center of the plane S is set at an origin of x-y coordinates.

Also, it is assumed that for the sake of convenience of description, m and n are even numbers and a size of one picture element is a square of $\Delta \times \Delta$.

Further, it is assumed that X-ray beams passing through the pseudo-tomographic plane S are projected in parallel from two directions fulfilling a relation of $\theta_1 = \tan^{-1} m$ and $\theta_2 = \pi/2$ and a beam diameter of each of the unit X-ray beams is sufficiently small compared to that of each of the picture elements.

The following equation may be provided when both the number of m of the first projectional densities $d_1(1)$ to $d_m(1)$ and the number of m of the second projectional densities $d_1(2)$ to $d_m(2)$ are applied so as to calculate the X-ray absorption coefficients $\mu_1$ to $\mu_m$ of each of the picture elements 1 to m in the first group of picture elements $Q_1$.

$$\mathbb{L}_p \mu = \mathbb{D}_{Q_1} \qquad (12)$$

where, $$\mathbb{L}_p = \left[ \begin{array}{cccccc} 1 & & & & & \\ 1 & 1 & & & 0 & \\ 1 & 1 & 1 & & & \\ \cdot & \cdot & \cdot & \cdot & & \\ \cdot & \cdot & \cdot & \cdot & \cdot & \\ \cdot & \cdot & \cdot & \cdot & \cdot & \cdot \\ 1 & \cdot & \cdot & \cdot & \cdot & 1 \\ 1 & \cdot & \cdot & \cdot & \cdot & 1 \\ 1 & \cdot & \cdot & \cdot & \cdot & 1 \\ 1 & \cdot & \cdot & \cdot & \cdot & 1 \\ \cdot & \cdot & \cdot & \cdot & \cdot & \cdot \\ \cdot & \cdot & \cdot & \cdot & \cdot & \cdot \\ \cdot & \cdot & \cdot & \cdot & \cdot & \cdot \\ 1 & \cdot & \cdot & \cdot & \cdot & 1 \end{array} \right] \begin{array}{c} \left.\rule{0pt}{3em}\right\} m \\ \left.\rule{0pt}{5em}\right\} m \end{array} \qquad (13)$$

$$\mu = (\mu_1, \mu_2, \mu_3, \cdots, \mu_m)^T$$

$$\mathbb{D}_{Q_1} = (d_1(1)/\alpha, d_2(1)/\alpha, \cdots, d_m(1)/\alpha, d_1(2), d_2(2), \cdots, d_m(2))^T$$

and $\mathbb{L}_p$ is a matrix of $2m \times m$.

$\alpha$ is a length of X-ray beams passing through one picture element in the direction $\theta_1$ and fulfills a relation of $$\alpha = \Delta \sqrt{1 + \cot^2 \theta_1}$$

and a symbol T is a transposition.

Resolving the equation (12) with a method of least squares may enable a calculation of the X-ray absorption coefficients $\mu_1$ to $\mu_m$ of each of the picture elements 1 to m in the first group of picture elements $Q_1$.

However, in general the data contain some measuring errors, so that when an answer for making an object function of $$F = \sum_{k=1}^{2m} r_k \qquad (14)$$

minimum is calculated by a mathematical programming under an equation of restrictive condition substantially the same as that of the equation (3) by introducing the non-negative correction values $r_1, r_2, r_3 \ldots r_{2m}$, resulting in that the most suitable two-dimensional data $\mu_1$ to $\mu_m$ may be calculated after a limited times of calculation.

Provided that the suffix i of $l_{i,j}, \mu_j, r_i, p_i$ in said equation (3) is 1, 2, 3, ... 2m, and the suffix j is 1, 2, 3, ... m.

In the above example, the two-dimensional data $\mu_1$ to $\mu_m$ of a tomogram have been calculated in reference to the object function for making a sum of absolute values of correction values in the equation of restrictive conditions minimum, there is also another method in which the object function of the above described equation (6) is made to be minimum on the basis of the equation of restrictive condition being substantially the same as that of the equation (5).

Also provided in this case that the suffix i of $l_{i,j}$, $\mu_j$, $p_i$ in said equation (5) is 1, 2, 3, ..., 2m, and the suffix j is 1, 2, 3, ... m.

In reference to this, two-dimensional tomographic data $\mu_1$ to $\mu_m$ of the X-ray tested tissue B are calculated under such conditions as the maximum correction value of the absolute value in said equation of restrictive conditions is minimum.

Further, it is possible to perform a calculation either by a method for making an object function of $$F = \sum_{k=1}^{2m} r_k^2 \qquad (15)$$

minimum under an equation of restrictive condition of the preferred embodiment corresponding to said equation (3) or by a method for making an object function of $$F = r^2 \qquad (16)$$

minimum under an equation of restrictive condition of the preferred embodiment corresponding to the equation (5).

Two-dimensional data $\mu_1$ to $\mu_m$ thus obtained are transmitted to the memory for three-dimensional structure G (memory) applied as a memory means, respectively.

Applying the number of m of the first projectional densities $d_{m+1}(1)$ to $d_{2m}(1)$, the number of m of the second projectional densities $d_{m+1}(2)$ to $d_{2m}(2)$ and thus obtained X-ray absorption coefficients in order to calculate the X-ray absorption coefficients $\mu_{m+1}$ to $\mu_{2m}$ of each of the picture elements m+1 to 2m in the second group of picture elements $Q_2$ may enable a calculation of the number of m of the X-ray absorption coefficients $\mu_{m+1}$ to $\mu_{2m}$ substantially in the same manner as described above.

As described above, the two-dimensional data $\mu_{m+1}$ to $\mu_{2m}$ are calculated, then these two-dimensional data $\mu_{m+1}$ to $\mu_{2m}$ are transmitted to the memory G.

The X-ray absorption coefficient of each of the picture elements in the subsequent third to n-th groups of picture elements $Q_3$ to $Q_n$ may be calculated by repeating the substantial similar operation.

In turn, the memory device for storing the three-dimensional internal structure G applied as a memory means is, as described above, constructed such that the signals from the dimensional transformer for projectional distribution F may be stored in order to construct each of the groups of picture elements $Q_1$ to $Q_n$ upon receiving a set of the number m of the signals from the dimensional transformer for projectional distribution F in reference to their relative orders, i.e. to construct the first n of the groups of picture elements from their left side in accordance with their sequential order, and further constructed such that the data for three-dimensional internal structure of the X-ray tested tissue B are calculated.

That is, the two-dimensional data $\mu_k$ (k=1, 2, 3, ..., mn) transmitted from the dimensional transformer for projectional distribution F in sequence by a set n of the number of m are related to the tomography of the X-ray tested tissue B, it is possible to get other projectional distributions of X-ray $D_1'$ and $D_2'$ by changing the measuring points with the measuring apparatus for projectional distribution of X-ray E, and thereby the two-dimensional data $\mu_k'$ for other tomographic planes may easily be obtained, so that it becomes possible to store the three-dimensional internal structure of the X-ray tested tissue of body B by accumulating the two-dimensional data $\mu_k$, $\mu_k'$, $\mu_k''$ ... for some different tomographic planes. However, in order to construct a complete three-dimensional internal structure, it will be needed to apply an interpolation between each of the tomographic data, so that the present memory G may be applied as a memory device having a calculation function.

It is the same as that of each of the preferred embodiments that to this memory G is connected the display of computed tomography of arbitrary transverse section J via the computed tomography reconstruction apparatus of arbitrary transverse section H, the improving apparatus for image quality of arbitrary transverse section I and D/A converter F'.

In order to reconstruct a tomography of the X-ray tested tissue B in reference to the above described arrangement, the first one-dimensional data $d_k(1)$ (major data) in the first projectional distribution of X-ray $D_1$ produced by X-ray detector C by projecting at first X-ray from X-ray source A toward the X-ray tested tissue B in a desired direction $\theta_1$ is calculated by measuring each of the values $d_k(1)$ at the number mn of the positions equally spaced apart with each other by a space w from one end of the first projectional distribution of X-ray $D_1$ to the other end of said first projectional distribution of X-ray $D_1$ by using the measuring means for the projectional distribution of X-ray E, and the second one-dimensional data (sub-data) $d_k(2)$ in the second projectional distribution of X-ray $D_2$ produced by X-ray detector C by projecting X-ray from X-ray source A toward the X-ray tested tissue B in another desired direction $\theta_2$ is calculated by measuring each of the values $d_k(2)$ at the number of mn of the positions equally spaced apart with each other by a space w from one end of said second projectional distribution of X-ray $D_2$ to the other end of said second projectional distribution of X-ray $D_2$ by using the measuring means for the projectional distribution of X-ray E.

Then, these one-dimensional data $d_k(1)$, $d_k(2)$ are properly converted from their analogue form to digital form, and the X-ray absorption coefficient of each of a set of the number m of the groups of the picture elements is calculated by the above described method in the dimensional transformer of X-ray F, and these X-ray absorption coefficients are transmitted in sequence to the memory G, thereby each of the X-ray absorption coefficients $\mu_k$ (two-dimensional data) of the number of mn of the picture elements in the pseudo-tomographic plane S is calculated, and these X-ray absorption coefficients are stored in the memory G in the specified order.

Then, these two-dimensional data $\mu_k$ are reconstructed and displayed as a tomography of the X-ray tested tissue of body B by the display of computed tomography of arbitrary transverse section J from the memory G via the computed tomography reconstruction apparatus of arbitrary transverse section H, the improving apparatus for image quality of arbitrary transverse section I and D/A converter F'.

Figure 8:
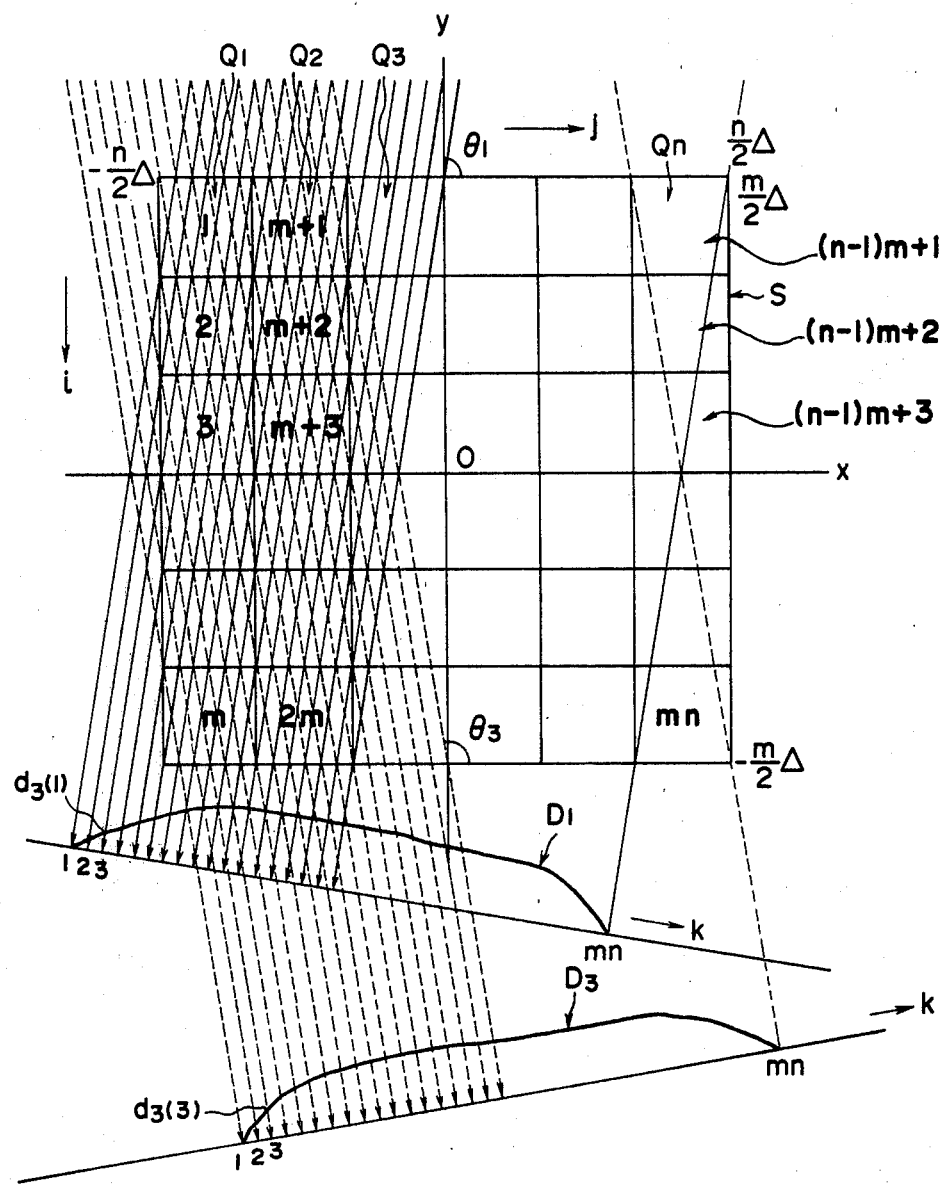
FIG. 8 is a schematic illustration for showing a reconstruction method of X-ray computed tomography in a fifth preferred embodiment of the present invention.

FIG. 8 is a schematic view for illustrating a reconstruction method of X-ray computed tomography of a fifth preferred embodiment of the present invention, wherein the similar numbers in FIG. 8 substantially correspond to that of FIGS. 2 to 7.

In the fifth preferred embodiment of the present invention, it is also assumed that the pseudo-tomographic plane S applied as a reconstruction plane for the tomography of the X-ray tested tissue of body B (the plane S is constituted by a set of n of the groups of picture elements constituted by the number of m of picture elements) is constituted by the number of mn of the small divided picture elements 1 to mn, as shown in FIG. 8, a center of the plane S is set at an origin of x-y coordinates, and the numbers m and n are, for convenience of description, an even number, respectively, and a size of one picture element is a square $\Delta \times \Delta$.

Further, it is assumed that the X-ray beams passing through the pseudo-tomographic plane S are, as similar to that of the second preferred embodiment, projected in parallel by the number of mn from two directions fulfilling a relation of $\theta_1 = \tan^{-1} m$ and $\theta_3 = -\tan^{-1} m$.

Further, it is assumed that a diameter of each of the unit X-ray beams is sufficiently small compared with that of each of the picture elements.

The following equation may be provided when the number m of the projectional densities $d_1(1)$ to $d_m(1)$ projected from a direction $\theta_1$ and the number of m of the projectional densities $d_1(3)$ to $d_m(3)$ projected from a direction $\theta_3$ are applied in order to calculate the X-ray absorption coefficients $\mu_1 \dots \mu_m$ for each of the picture elements 1 to m in the first groups of picture elements $Q_1$.

$$L'_P \mu = D_{Q'_1} \tag{17}$$

where $$L'_P = \begin{pmatrix} 1 & & & & & & \\ 1 & 1 & & & & & \\ 1 & 1 & 1 & & 0 & & \\ \vdots & & & \ddots & & & \\ 1 & \cdots & \cdots & \cdots & \cdots & 1 & \\ & & & & & & 1 \\ & & & & & 1 & 1 \\ & 0 & & 1 & 1 & 1 & \\ & & & \vdots & & & \\ 1 & \cdots & \cdots & \cdots & \cdots & 1 & \end{pmatrix} \begin{matrix} \Big\} m \\ \\ \Big\} m \end{matrix}$$

$$\underbrace{\phantom{xxxxxxxxxxxx}}_{m} \tag{18}$$

$$\mu = (\mu_1, \mu_2, \mu_3, \dots, \mu_m)^T$$

$$D_{Q'_1} = (d_1(1), d_2(1), \dots, d_m(1), d_1(3), d_2(3), \dots, d_m(3))^T / \alpha$$

$L'_P$ is a matrix of $2m \times m$.

A value of α is a length of X-ray beams passing through one picture element in the directions $\theta_1$ and $\theta_3$, and fulfills a relation of $$\alpha = \Delta \sqrt{1 + \cot^2 \theta_1} = \Delta \sqrt{1 + \cot^2 \theta_3}$$

and a symbol T indicates a transposition.

Resolving the equation (17) by a method of least squares may enable a calculation for the two-dimensional tomographic data $\mu_1$ to $\mu_m$ of the X-ray tested tissue B substantially in the same manner as that of each of the preferred embodiments. However, in general, the data have some measuring errors, so that the errors found in case of performing a reconstruction are made to be minimum by applying a mathematical programming in the same manner as that of each of the preferred embodiments.

The signals corresponding to the X-ray absorption coefficients $\mu_1$ to $\mu_m$ of the X-ray applied as the two-dimensional data thus obtained are transmitted to the memory G.

In sequence, substantially in the same manner as above, the X-ray absorption coefficient of each of the picture elements is calculated for the second to n-th of the groups of picture elements $Q_2$ to $Q_n$, and further these X-ray absorption coefficients are transmitted to the memory G, the X-ray absorption coefficients are stored in the memory G under the specified order.

Then, these two-dimensional data $\mu_k$ (k=1, 2, ..., mn) are reconstructed and displayed as a tomogram of the X-ray tested tissue B by the display of computed tomography of arbitrary transverse section J from the memory G via computed tomography reconstruction apparatus of arbitrary transverse section H, the improving apparatus for image quality of arbitrary transverse section I and D/A converter F'.

Figure 9:
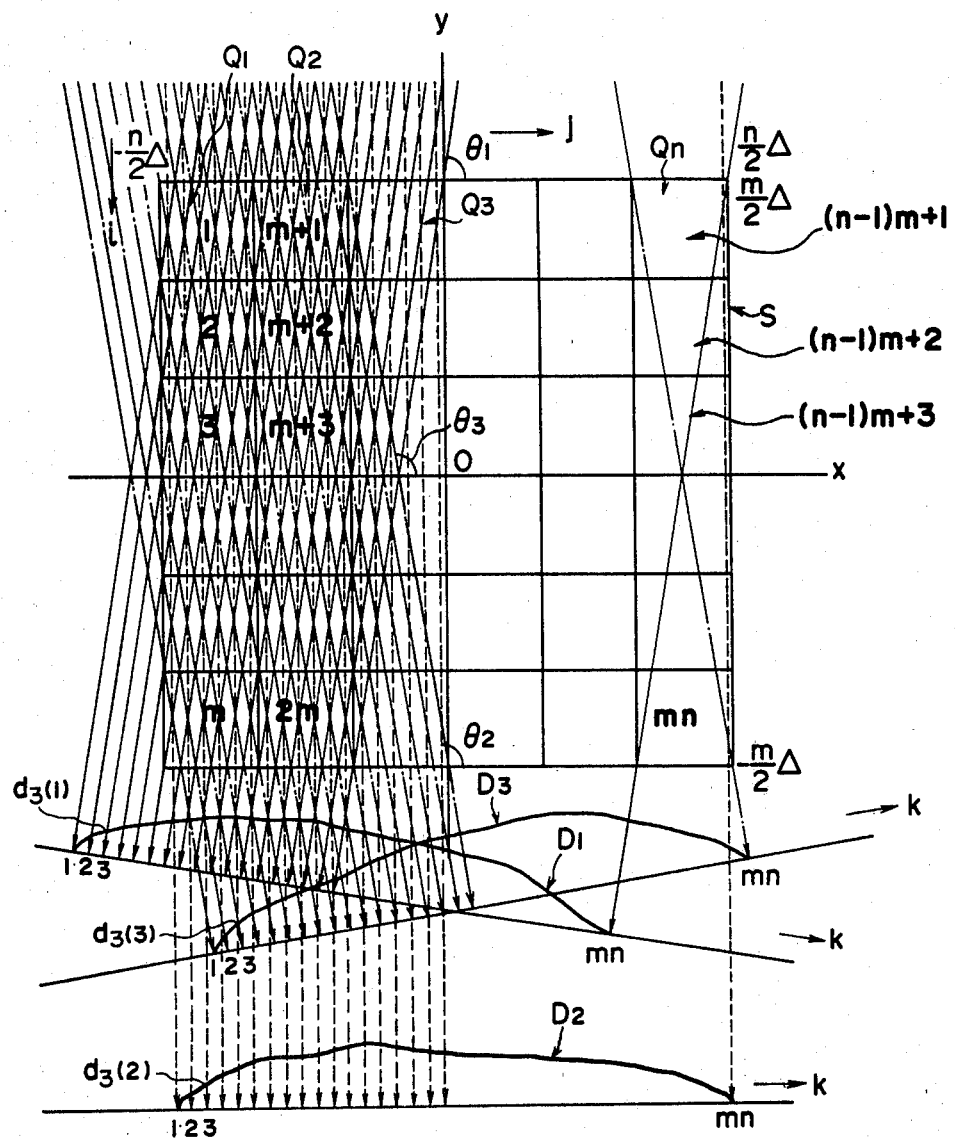
FIG. 9 is a schematic illustration for showing a reconstruction method of X-ray computed tomography in a sixth preferred embodiment of the present invention.

FIG. 9 is a schematic view for illustrating a reconstruction method of X-ray computed tomography of a sixth preferred embodiment of the present invention, wherein the similar numbers in FIG. 9 substantially correspond to that of FIGS. 2 to 8.

The sixth preferred embodiment is the same as that of the above described preferred embodiments, and in this case, it is assumed that, as shown in FIG. 9, the pseudo-tomographic plane S applied as a reconstruction plane of the tomography of the X-ray tested tissue B (this plane S being constructed by a set n of the groups of picture elements constituted by the number m of the picture elements) is constituted by the number mn of the small divided picture elements 1 to mn, a center of the plane S is placed at an origin of x-y coordinates, and for a convenience of description, the numbers m and n are even numbers, a size of one picture element is a square of $\Delta \times \Delta$.

Further, it is assumed that the X-ray beams passing through the pseudo-tomographic plane S are projected or emitted in parallel by the number mn from three directions fulfilling a relation of $\theta_1 = \tan^{-1} m$, $\theta_2 = \pi/2$ and $\theta_3 = -\tan^{-1} m$ in the same manner as that of said third preferred embodiments.

It is assumed that a diameter of each of the unit X-ray beams is sufficiently small compared with that of each of the picture elements.

Applying the number m of the projectional densities $d_1(1)$ to $d_m(1)$ under a projected direction of $\theta_1$, the number of m of the projectional densities $d_1(2)$ to $d_m(2)$ under a projected direction of $\theta_2$ and the number m of the projectional densities $d_1(3)$ to $d_m(3)$ may provide the following equation in order to calculate the X-ray absorption coefficients $\mu_1$ to $\mu_m$ of each of the picture elements 1 to m in the first group of the picture elements $Q_1$.

$$\mathbb{L}''_p \mu = \mathbb{D}''_{Q1} \quad (19)$$

where, $$\mathbb{L}''_p = \begin{pmatrix} 1 & & & & & \\ 1 & 1 & & & & \\ 1 & .1 & 1 & & 0 & \\ \vdots & \vdots & \vdots & \vdots & & \\ \vdots & \vdots & \vdots & \vdots & & \\ 1 & \cdots & \cdots & \cdots & 1 & \\ 1 & \cdots & \cdots & \cdots & 1 & \\ \vdots & \vdots & \vdots & \vdots & & \\ \vdots & \vdots & \vdots & \vdots & & \\ 1 & \cdots & \cdots & \cdots & 1 & \\ & & & & 1 & 1 \\ & 0 & & & 1 & 1 & 1 \\ & & & & \vdots & \vdots & \vdots \\ & & & & \vdots & \vdots & \vdots \\ 1 & \cdots & \cdots & \cdots & 1 & \end{pmatrix} \begin{matrix} \} m \\ \\ \\ \} m \\ \\ \\ \} m \end{matrix}$$

$$\cdots \cdots (20)$$

$$\mu = (\mu_1, \mu_2, \mu_3, \cdots, \mu_m)^T$$

$$\mathbb{D}''_{Q1} = (d_1(1)/\alpha, d_2(1)/\alpha, \cdots, d_m(1)/\alpha,$$
$$d_1(2), d_2(2), \cdots, d_m(2),$$
$$d_1(3)/\alpha, d_2(3)/\alpha, \cdots, d_m(3)/\alpha)^T$$

and $\mathbb{L}''_p$ is a matrix of 3 m × m.

And a value of α shows a length of X-ray beams passing through one picture element in the directions $\theta_1$ and $\theta_3$ and fulfills a relation of $$\alpha = \Delta \sqrt{1 + \cot^2 \theta_1} = \Delta \sqrt{1 + \cot^2 \theta_3}$$

and a symbol T shows a transposition.

Resolving this equation (19) by a method of least squares may enable a calculation of the two-dimensional tomographic data $\mu_1$ to $\mu_m$ of the X-ray tested tissue B substantially in the same manner as that of each of the preferred embodiments. However, in general, the data contain some measuring errors, so that it is performed to make the errors in case of reconstruction minimum by applying a mathematical programming substantially in the same manner as that of each of the above mentioned preferred embodiments.

The signals corresponding to the X-ray absorption coefficients $\mu_1$ to $\mu_m$ of the two-dimensional data thus obtained are transmitted to the memory G.

X-ray absorption coefficients for each of the picture elements in subsequent orders of 2 to n of the groups of picture elements $Q_2$ to $Q_n$ will be calculated under the substantial similar operation, and will be transmitted in sequence to the memory G, then the X-ray absorption coefficients may be stored in the memory G under a specified order.

Thereafter, these two-dimensional data $\mu_k$ (k=1, 2, ..., mn) are reconstructed and displayed as a tomography of the X-ray tested tissue B by the display of computed tomography of arbitrary transverse section J from the memory G via computed tomography reconstruction apparatus of arbitrary transverse section H, the improving apparatus for image quality of arbitrary transverse section I and D/A converter F'.

Further, as shown in each of the fourth to sixth preferred embodiments, in place of constructing a partial plane of columns of the tomography of the X-ray tested tissue B by each of the groups of the picture elements constituted by the number m of the picture elements, it may be performed such that the groups of picture elements constituted by the number 2 m to m (n−1) of the picture elements are properly combined with each other to construct the partial plane of columns of the tomography.

Further, these groups of picture elements may be constituted by the number m to m (n−1) of picture elements in order to form a partical plane of columns of the tomography by each of the groups of picture elements, and in addition to this, these groups of picture elements may be constituted by the number of n to (m−1)n of picture elements in order to make a partial plane of rows of said tomography.

Each of the groups of picture elements may be constituted by the picture elements which numbers are less than m and n.

Further, that is, one group of picture elements may be constituted by any number of picture elements if they are less than the number mn but it is preferable that the number of picture elements constituting one group of picture elements is defined or set to the most suitable number in reference to a capacity of data processing device and a data processing time.

When it is selected that the groups of picture elements form a partial plane of rows of the tomography different from that of the above described fourth and fifth preferred embodiments, it may be possible to apply some values of $\tan^{-1} n$, 0 or $\tan^{-1} n$, $-\tan^{-1} n$ as an example of two projectional directions, and even in case of this such an example above, it is possible to calculate the number mn (=N) of the X-ray absorption coefficients and reconstruct the tomography of the X-ray tested tissue of body substantially in the same manner as that of each of the preferred embodiments.

Further, when it is selected that the groups of picture elements form a partial plane of columns of the tomography different from that of the above described sixth preferred embodiment, it may be possible to apply some values of $\tan^{-1} n$, $-\tan^{-1} n$ and 0 as an example of three projectional directions, and even in case of this such an example as above, it is possible to calculate the number mn (=N) of the X-ray absorption coefficients and reconstruct the tomography of the X-ray tested tissue of body substantially in the same manner as that of each of the preferred embodiments.

Further, a tomography may be reconstructed in the same way as above even if the direction of projecting X-ray shows more than three directions, and the increased number of projecting directions of X-ray may enable an improving of the accuracy as well as cause data processing time to be increased and make hardware for the system large. In view of this fact, the number of projecting directions of X-rays may be determined.

And as illustrated in the above described fourth to sixth preferred embodiments, each of the number of N of one-dimensional data is measured from one of a plurality of projectional distributions of X-rays and also each of the number of N one-dimensional data is measured from the remaining projectional distributions of X-rays. Instead of this measuring method as above, it is also possible to calculate the X-ray absorption coefficient applied as two-dimensional data in reference to these one-dimensional data by measuring each of the number of N of one-dimensional data from the one projectional distribution of X-rays and further measuring each of a proper number (which may be more than or less than the number N) of one-dimensional data from said remaining projectional distributions of X-rays.

In case of applying the projecting X-ray beams of which projecting directions are $\pi/2$ or 0, it may also be possible to have an added value multiplied by the number m or n against the object function during the calculation process by a method in which a partial plane of each of the columns or a partial plane of each of the rows of the pseudo-tomographic plane is expressed by a mean value of the number m or n of the beams, resulting in that a saving the memory or a shortened time required for calculation may be provided.

Figure 10:
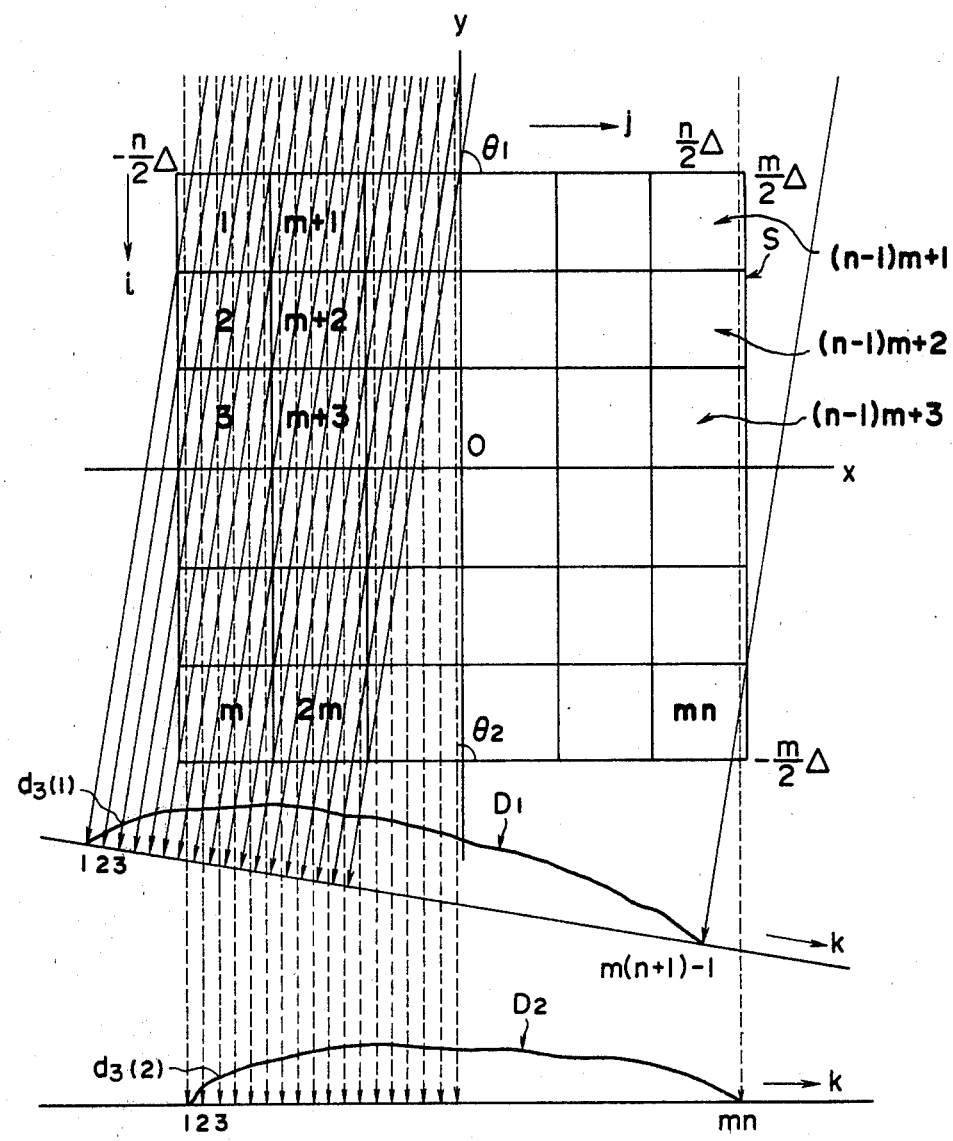
FIG. 10 is a schematic illustration for showing a reconstruction method of X-ray computed tomography in a seventh preferred embodiment of the present invention.

FIG. 10 is a schematic view for illustrating a reconstruction method of X-ray computed tomography of a seventh preferred embodiment of the present invention wherein the similar numbers in FIG. 10 substantially correspond to that of FIGS. 2 to 9.

In the seventh preferred embodiment, each of a plurality M of the values $d_k(1)$ in the first projectional distribution of X-rays $D_1$ and each of a plurality of mn of the values $d_k(2)$ in the second projectional distribution of X-rays $D_2$ produced by projecting X-ray from the desired two directions toward the X-ray tested tissue of body B are calculated by the first means constituted by the measuring means for projectional distribution of X-ray E and A/D converter F' etc., then the data outputs $d_k(1)$, $d_k(2)$ (digital signals) produced from the first means are fed to the dimensional transformer for projectional distribution F constituting the second means, respectively.

The dimensional transformer for projectional distribution F calculates and feeds out the signals corresponding to each of the X-ray absorption coefficients $\mu_t$ (two-dimensional data) of the number of mn (=N<M) of the picture elements constituting the pseudo-tomographic plane S containing a tomographic plane of the X-ray tested tissue B in reference to the data output $d_k(1)$ (one-dimensional data; major data) of the number of m(n+1)31 1 (=M) of the first projectional distribution of X-ray produced from said first means and to the data output $d_k(2)$ (one-dimensional data; sub-data) of the number mn of the second projectional distribution of X-ray. As its practical or actual example, a digital computer storing the desired programs may be applied.

Then, a method will be described in which each of the X-ray absorption coefficients $\mu t$ (two-dimensional data) for the number of N of the picture elements as the constituent component elements of the pseudo-tomographic plane S containing a tomographic plane of the X-ray tested tissue B is calculated in reference to each of the groups of the measured values constituted by the number M of the measured values $d_k(1)$ (one-dimensional data) in the first projectional distribution of X-ray $D_1$ produced by the first means and also to each of the groups of the measured values constituted by the number N of the measured values $d_k(2)$ (one-dimensional data) in the second projectional distribution of X-ray $D_2$ produced by the first means substantially in the same manner as above.

At first, it is assumed that the pseudo-tomographic plane S applied as a reconstruction plane for a tomography of the X-ray tested tissue B is, as shown in FIG. 10, made by the number mn (=N) of picture elements applied as the small divided picture elements, and a center of the plane S is placed at an origin of x-y coordinates.

Further, for a convenience of description, the numbers m and n are an even number and a size of one picture element is a square of $\Delta \times \Delta$.

Further, it is assumed that X-ray beams passing through the pseudo-tomographic plane S are projected in parallel from such two directions as fulfilling $\theta_1 = \tan^{-1} m$ and $\theta_2 = \pi/2$, and a diameter of each of the unit X-ray beams is sufficiently small compared with that of each of the picture elements.

If it is assumed that each of the picture elements is provided with a number in accordance with the order as shown in FIG. 10, the absorption coefficient of the picture element is defined by $\mu_t$, the X-ray beam is projected from a direction of $\theta_1$, a projection density made by the first unit X-ray beam passing through a point $(x_j, y_i)$ in x-y coordinates is defined as $d_k(1)$ and the following equation may be provided.

$$x_j = \left(-\frac{n}{2} + j - 1\right) \cdot \Delta, \quad y_i = \left(\frac{m}{2} - i\right) \cdot \Delta,$$

$$t = (j-1) \cdot m + i,$$

(i=1, 2, ..., m; j=1, 2, ..., n), $$k = (j-1) \cdot m + i, \text{ provided } k \neq mn + m$$

(i=1, 2, ..., m; j=1, 2, ..., n+1), where, i is a row and j is a column.

And further if it is assumed that the projectional density produced by the second unit X-ray beam in a direction from $\theta_2$ is expressed by $d_k(2)$, the following equation may be provided.

And it is assumed that the X-ray beam projected from a direction $\theta_2$ is to be projected from a relation of $x_0 = \Delta/2 \, (-n + 1/m)$ with an equal space of $w = \Delta/m$ $$\mathbb{L}_k \mu = {}^1D_A \qquad (21)$$

where

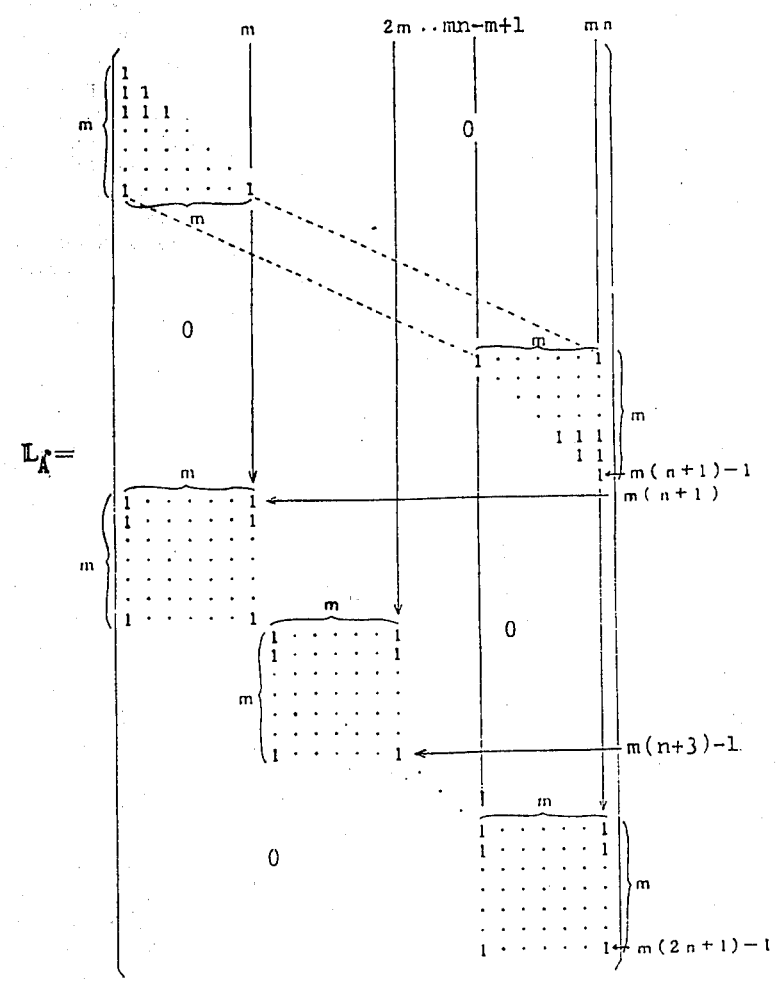

$$\cdots\cdots\cdots\cdots\cdots\cdots \quad (22)$$

$\mu = (\mu_1, \mu_2, \mu_3, \ldots, \mu_{mn})^T$ $\mathbb{D}_A = (d_1(1)/\alpha, d_2(1)/\alpha, \ldots, d_{m(n+1)-1}(1)/\alpha,$ $\qquad d_1(2), d_2(2), \ldots, d_{mn}(2))^T$ $\mathbb{L}_A$ is a matrix of $(2\,mm+M-1) \times mn$ A value of $\alpha$ is a length of an X-ray beam passing through one picture element from a direction of $\theta_1$ and fulfills an equation of $$\alpha = \Delta \sqrt{1 + \cot^2 \theta_1}$$

and the symbol T represents a transpose. And for a sake of convenience of description, a relation of $2\,mn+m-1=M'$ is applied.

In turn, in the equation (21) it is found that the number M' of the equation is larger than the number N of the X-ray absorption coefficient $\mu_t$ applied as an unknown value and the most suitable value of the X-ray absorption coefficient $\mu_t$ as the unknown value is to be calculated. In order to perform the calculation, a method of least square may be applied.

Thus, applying the method of least square to the equation (21) may result in that a transpositioned matrix of is multiplied to both sides of the equation (21) from their left ones and the following equation may be provided.

$$\mathbb{L}_A^T \mathbb{L}_A \mu = \mathbb{L}_A^T \cdot \mathbb{D}_A \qquad (23)$$

The equation (23) thus obtained shows that the number of the unknown value is equal to that of the equation, so that resolving this equation (23) may calculate the two-dimensional tomographic data $\mu_t$ of the x-ray tested tissue of body. However, in general, the data contain some measuring errors.

Thus, non-negative correction values of $r_1, r_2, r_3 \ldots r_{M'}$ are applied and a restrictive equation substantially the same as the equation (3) is allied to calculate, under a mathematical programming, a solution or an answer for making an object function of $$F = \sum_{k=1}^{M'} r_k \qquad (24)$$

minimum, resulting in showing the two-dimensional data $\mu_t$ after the calculation of limited times.

Provided that the suffix i of $l_{i\cdot j}$, $\mu_j$, $r_i$, $p_i$ in said equation (3) is $1, 2, 3, \ldots, M'$, and the suffix j is $1, 2, 3, \ldots, N$.

In the above example, the two-dimensional data $\mu_t$ have been calculated in reference to the object function for making a sum of absolute values of correction values in the equation of restrictive conditions minimum, there is also another method in which the object function of the above described equation (6) is reduced to a minimum on the basis of the equation of restrictive condition being substantially the same as that of the equation (5).

Also provided in this case that the suffix i of $l_{i\cdot j}$, $\mu_j$, $p_i$ in said equation (5) is $1, 2, 3, \ldots, M'$, and the suffix j is $1, 2, 3, \ldots, N$.

In reference to this, two-dimensional tomographic data $\mu_t$ of the X-ray tested tissue of body are calculated under such conditions as the maximum correction value of the absolute value in the equation of restrictive conditions is minimum.

Further, it is possible to perform a calculation either by a method for making an object function of $$F = \sum_{k=1}^{M'} r_k^2 \qquad (25)$$

minimum under an equation of restrictive condition of the preferred embodiment corresponding to the equation (3) or by a method for making an object function of $$F = r^2 \qquad (26)$$

minimum under an equation of restrictive condition of the preferred embodiment corresponding to the equation (5).

Two-dimensional data $\mu_t$ thus obtained are transmitted to the memory for three-dimensional structure G, respectively.

The memory for three-dimensional structure G is operated such that the two-dimensional data $\mu_t$ for use in reconstructing a tomography which are transmitted from the dimensional transformer of projectional data F are stored in a time sequence and then the data of three-dimensional structure for the X-ray tested tissue B are calculated.

The two-dimensional data $\mu_t$ transmitted at first from the dimensional transformer of projectional data F show that of a certain tomographic plane of the X-ray tested tissue B, and it is possible to calculate another projectional distributions of X-ray $D_1'$ and $D_2'$ by changing a measuring point with the measuring apparatus for projectional distribution of X-ray E and also to facilitate a calculation of the two-dimensional data $\mu_t'$ concerning other tomographic planes, so that three-dimensional internal structure of the X-ray tested tissue B may be stored by accumulating the two-dimensional data $\mu_t, \mu_t', \mu_t'' \ldots$ concerning some different tomographic planes. However, in order to make a complete three-dimensional internal structure, it will become necessary to have an interpolation etc. between each of the tomographic data and in view of this fact, the present memory G is used as a memory device having a calculation function for performing the interpolation etc.

It is the same as that of each of the preferred embodiments that to this memory G is connected the display of computed tomography of arbitrary transverse section J via the computed tomography reconstruction apparatus of arbitrary transverse section H, the improving apparatus for image quality of arbitrary transverse section I and D/A converter F'.

In order to reconstruct a tomogram of the X-ray tested tissue B in reference to the above described arrangement, the first one-dimensional data (major data) $d_k(1)$ in the first projectional distribution of X-ray $D_1$ produced by X-ray detector C by projecting at first X-rays from X-ray source A toward the X-ray tested tissue B in a desired direction $\theta_1$ is calculated by measuring each of the values $d_k(1)$ at the number $m(n+1)-1(=M)$ of the positions equally spaced apart with each other by a space w from one end of said first projectional distribution of X-rays $D_1$ to the other end of the first projectional distribution of X-rays $D_1$ by the measuring means for the projectional distribution of X-rays E, and the second one-dimensional data (sub-data) $d_k(2)$ in the second projectional distribution of X-ray $D_2$ produced by X-ray detector C by projecting X-ray from X-ray source A toward the X-ray tested tissue B in another desired direction $\theta_2$ is calculated by measuring each of the values $d_k(2)$ at the number mn ($=N'$) of the positions equally spaced apart with each other by a space w from one end of the first projectional distribution of X-ray $D_2$ to the other end of the second projectional distribution of X-ray $D_2$ by the measuring means for the projectional distribution of X-rays E.

Then, the number $M'$ (M+N) of these one-dimensional data $d_k(1)$, $d_k(2)$ are properly converted from their analogue form to digital form, and each of the X-ray absorption coefficients $\mu_t$ (two-dimensional data) of each of the number N ($<M'$) of the picture elements is calculated in the pseudo-tomographic plane S by the dimensional transformer of projectional data F with the above described method.

Then, these two-dimensional data $\mu_t$ are reconstructed and displayed as a tomogram of the X-ray tested tissue B by the display of computed tomography of arbitrary transverse section J via memory G, the computed tomography reconstruction apparatus of arbitrary transverse section H, the improving apparatus for image quality of arbitrary transverse section I and D/A converter F'.

Figure 11:
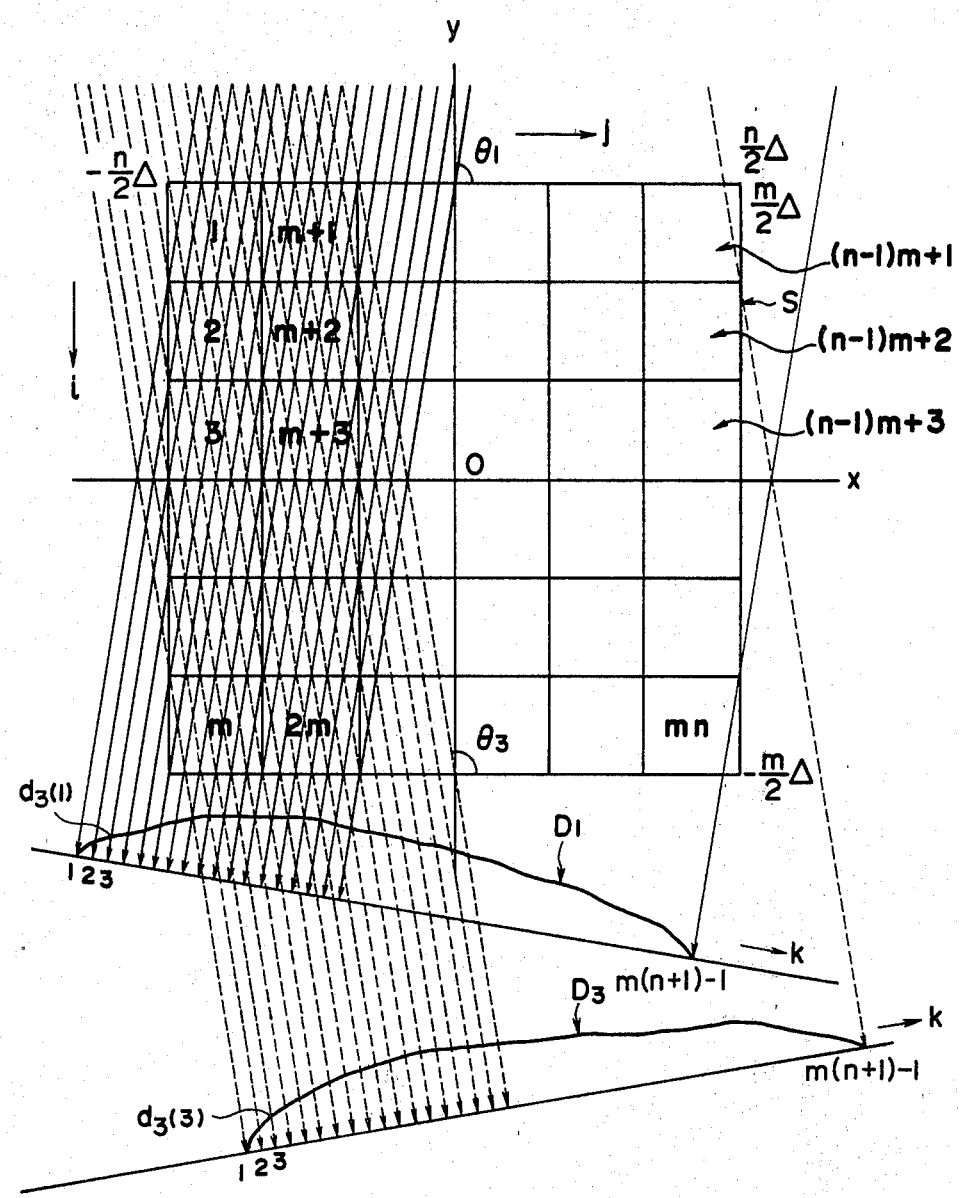
FIG. 11 is a schematic illustration for showing a reconstruction method of X-ray computed tomography in an eighth preferred embodiment of the present invention.

FIG. 11 is a schematic view for illustrating a reconstruction method of X-ray computed tomography of an eighth preferred embodiment of the present invention, wherein the similar reference numbers in FIG. 11 substantially correspond to that of FIGS. 2 to 10.

In this case, it is also assumed that, as shown in FIG. 11, the pseudo-tomographic plane S applied as a reconstruction plane of the tomogram of the X-ray tested tissue B is constituted by the number of mn of the small divided picture elements 1 to mn, a center of the plane S is placed at an origin of the x-y coordinates, and for a convenience of description, the numbers m and n are even numbers, a size of one picture element is a square of $\Delta \times \Delta$.

Further, it is assumed that the X-ray beams passing through the pseudo-tomographic plane S are projected in parallel in the number of $m(n+1)-1$ ($=M$) from two directions fulfilling a relation of $\theta_1 = \tan^{-1} m$ and $\theta_3 = -\tan^{-1} m$.

It is assumed that a diameter of each of the unit X-ray beams is sufficiently small compared with that of each of the picture elements.

In this way, the above mentioned equation (21) may be expressed as follows when the specified two directions for use in projecting the X-ray are set at $\theta_1$ and $\theta_3$.

$$\mathbb{L}_A^j \mu = \mathbb{D}_A^j \tag{27}$$

where

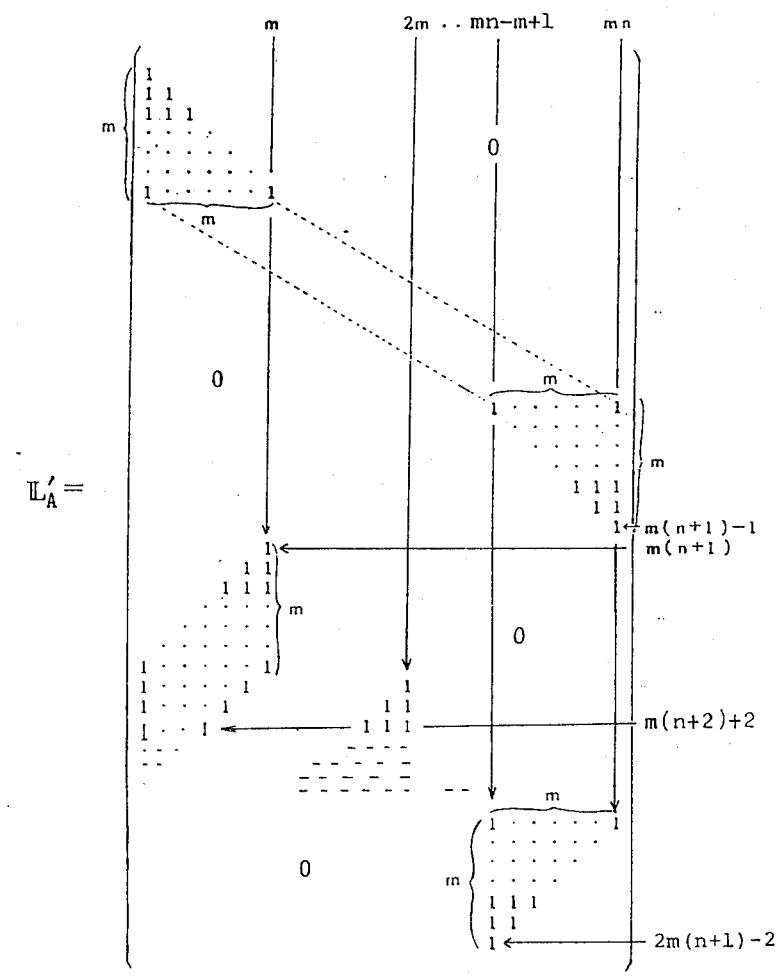

$$\cdots \cdots \cdots \cdots \cdots \cdots \cdots \tag{28}$$

$$\mu = (\mu_1, \mu_2, \mu_3, \ldots, \mu_{mn})^T$$

$$\mathbb{D}'_A = (d_1(1), d_2(1), \ldots, d_{m(n+1)-1}(1),$$

$$d_1(3), d_2(3), \ldots, d_{m(n+1)-1}(3))^T/\alpha'$$

In this equation, $d_k(1)$ is a measured value produced by projecting X-rays in a direction $\theta_1$, and $d_k(3)$ is a measured value produced by projecting X-rays in a direction $\theta_3$, respectively.

And a value of the $\alpha'$ shows a length of X-ray beams passing through one picture element in the directions $\theta_1$ and $\theta_3$ and fulfills a relation of $$\alpha' = \Delta \sqrt{1 + \cot^2 \theta_1} = \Delta \sqrt{1 + \cot^2 \theta_3}$$

and a symbol T shows a transposition.

Resolving this equation (27) by a method of least square may enable a calculation of the two-dimensional tomographic data $\mu_t$ of the X-ray tested tissue B substantially in the same manner as that of each of the preferred embodiments. However, in general, the data contain some measuring errors, so that it is performed to make the errors in case of reconstruction minimum by applying a mathematical programming substantially in the same manner as that of each of the above mentioned preferred embodiments.

The signals corresponding to the X-ray absorption coefficients $\mu_t$ of the two-dimensional data thus obtained are reconstructed and displayed as a tomogram of the X-ray tested tissue B by the display of computed tomography of arbitrary transverse section J from the memory G via computed tomography reconstruction apparatus of arbitrary transverse section H, the improving apparatus for image quality of arbitrary transverse section I and D/A converter F'.

In addition to the above described seventh and eighth preferred embodiments, it is possible to apply some values of $\tan^{-1} m$, 0, $\tan^{-1} m$ and $\pi/2 \pm \tan^{-1} m$ etc. Also in this case, it is possible to calculate the number of mn ($=N$) of the X-ray absorption coefficients substantially in the same manner as that of each of the preferred embodiments and reconstruct a tomogram of the X-ray tested tissue of a body.

Figure 12:
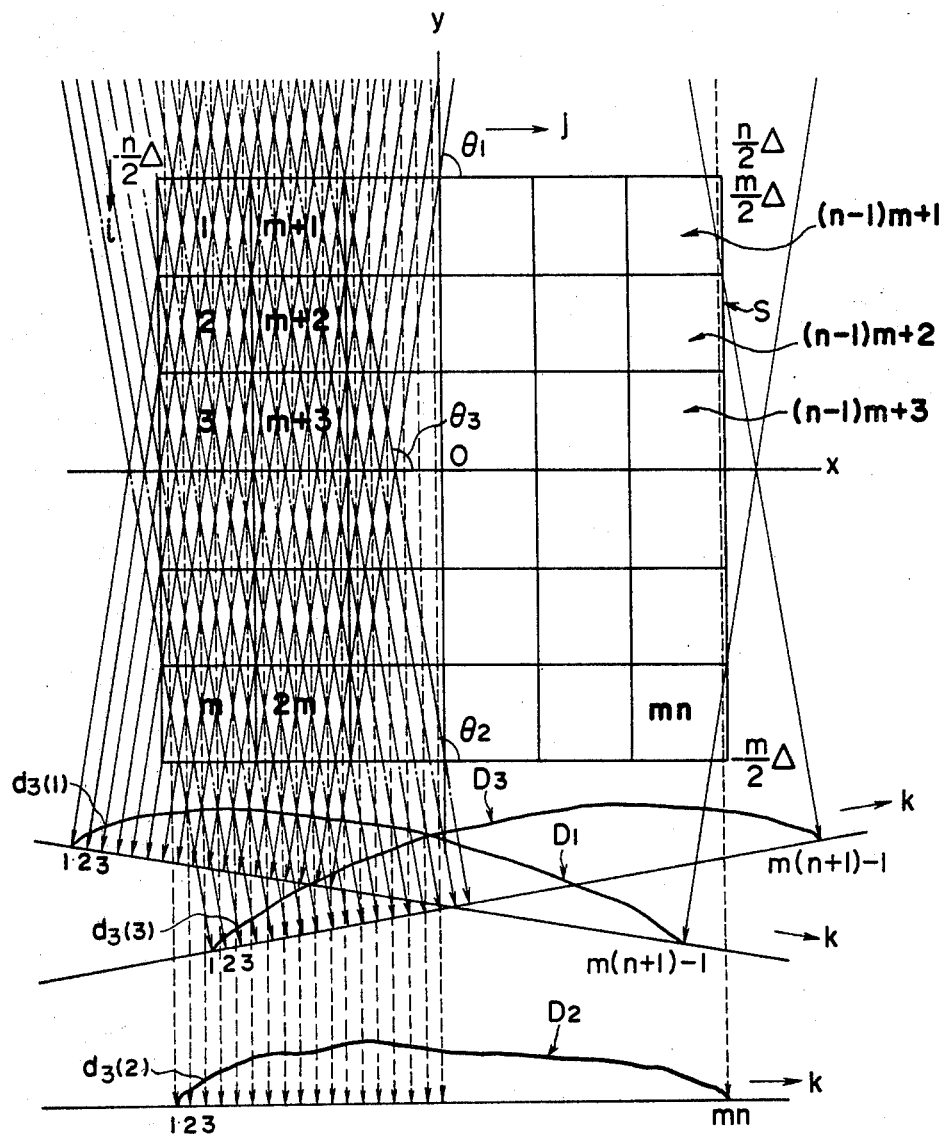
FIG. 12 is a schematic illustration for showing a reconstruction method of X-ray computed tomography in a ninth preferred embodiment of the present invention.

FIG. 12 is a schematic view for illustrating a reconstruction method of X-ray computed tomography of a ninth preferred embodiment of the present invention wherein the similar reference numbers in FIG. 12 substantially correspond to that of FIGS. 2 to 11.

Also in the ninth preferred embodiment, it is assumed that the pseudo-tomographic plane S applied as a tomography reconstruction plane of the X-ray tested tissue of body B is constituted by the number of mn of the small divided picture elements 1 to mn, as shown in FIG. 12, a center of the plane S is set at an origin of x-y coordinates, and for the sake of convenience of description, m and n are even numbers and a size of one picture element is a square of $\Delta \times \Delta$.

Further, it is assumed that X-ray beams passing through the pseudo-tomographic plane S are projected in parallel from three directions fulfilling a relation of $\theta_1 = \tan^{-1} m$, $\theta_2 = \pi/2$ and $\theta_3 = -\tan^{-1} m$ by the number m(n+1)−1 (=M), mn (=N) and m(n+1)−1 (=M).

Further, it is assumed that a beam diameter of each of the unit X-ray beams is sufficiently small compared to that of each of the picture elements.

In this way, when the desired three directions for use in projecting X-ray are set at such values as $\theta_1$, $\theta_2$ and $\theta_3$, the above described equation (21) may be expressed as follows;

$$\mathbb{L}''_A \mu = \mathbb{D}''_A \qquad (29)$$

where,

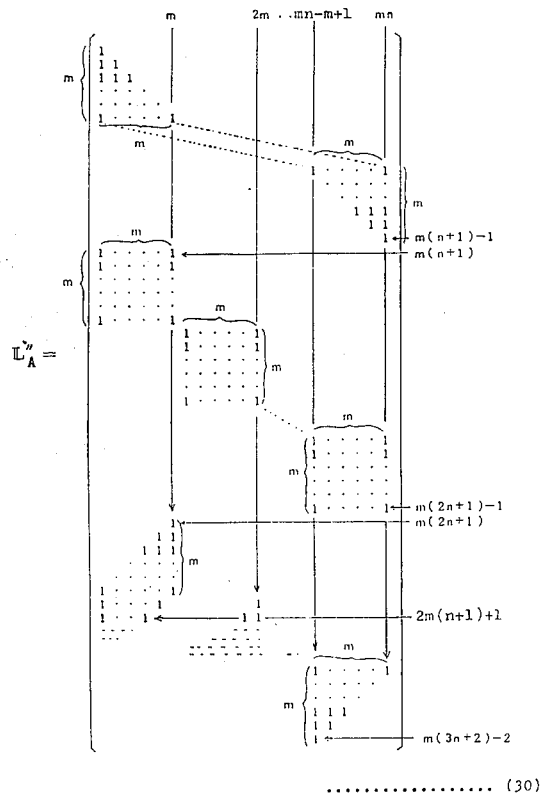

$$\ldots \ldots \ldots \ldots (30)$$

$$\mu = (\mu_1, \mu_2, \mu_3, \ldots, \mu_{mn})^T$$

$$\mathbb{D}''_A = (d_1(1)/\alpha', d_2(1)/\alpha', \ldots, d_{m(n+1)-1}(1)/\alpha',$$

$$d_1(2), d_2(2), \ldots, d_{mn}(2),$$

$$d_1(3)/\alpha', d_2(3)/\alpha', \ldots, d_{m(n+1)-1}(3)/\alpha')^T$$

Values of $d_k(1)$, $d_k(2)$ and $d_k(3)$ show the measured values produced by projecting X-ray from the directions of $\theta_1$, $\theta_2$ and $\theta_3$, respectively.

Resolving the equation (29) by a method of least squares may enable a calculation for the two-dimensional tomographic data $\mu_t$ of the X-ray tested tissue of body B substantially in the same manner as that of each of the preferred embodiments. However, in general, the data have some measuring errors, so that the errors found in case of performing a reconstruction are reduced to a minimum by applying a mathematical programming in the same manner as that of the above described preferred embodiments.

The signals corresponding to the X-ray absorption coefficients $\mu_t$ applied as the two-dimensional data thus obtained are transmitted to the memory G, and thereafter reconstructed and displayed as a tomogram of the X-ray tested tissue B by the display of computed tomography of arbitrary transverse section J from the memory G via computed tomography reconstruction apparatus of arbitrary transverse section H, the improving apparatus for image quality of arbitrary transverse section I and D/A converter F'.

In addition to the above described ninth preferred embodiment, it is possible to apply some values of $\tan^{-1} m$, $-\tan^{-1} m$, 0, and $\tan^{-1} m$, $\pi/2$, 0 etc. Also in this case, it is possible to calculate the number $mn$ ($=N$) of the X-ray absorption coefficients substantially in the same manner as that of each of the preferred embodiments and reconstruct a tomography the X-ray tested tissue of body.

Further, a tomography may be reconstructed in the same way as above even if the direction of projecting X-rays is more than three directions, and the increased number of projecting directions of X-rays may enable an improving of the accuracy as well as cause data processing time to be increased and make hardware for the system large. In view of this fact, the number of projecting directions of X-ray may be determined.

And as illustrated in the above described seventh to ninth preferred embodiments, each the number of M of one-dimensional data is measured from one of a plurality of projectional distributions of X-rays and each of the number N or M of one-dimensional data is measured from the remaining projectional distributions of X-rays. Instead of this measuring method as above, it is also possible to measure the number of M of each of one-dimensional data from the one projectional distribution of X-ray and a suitable number (which may be more than or less than the number N or M) of each of one-dimensional data from said remaining projectional distributions of X-rays and then calculate the X-ray absorption coefficient applied as two-dimensional data in reference to these one-dimensional data.

In case of applying the projecting X-ray beams of which projecting directions are $\tan^- \pi/2$ or 0, it may also be possible to have an added value multiplied by the number m or n against the object function during the calculation process by a method in which a partial plane of each of the columns or a partial plane of each of the rows of the pseudo-tomographic plane is expressed by a mean value of the number m or n of the beams, resulting in that a saving of the memory or a shortened time required for calculation may be obtained.

Figure 13:
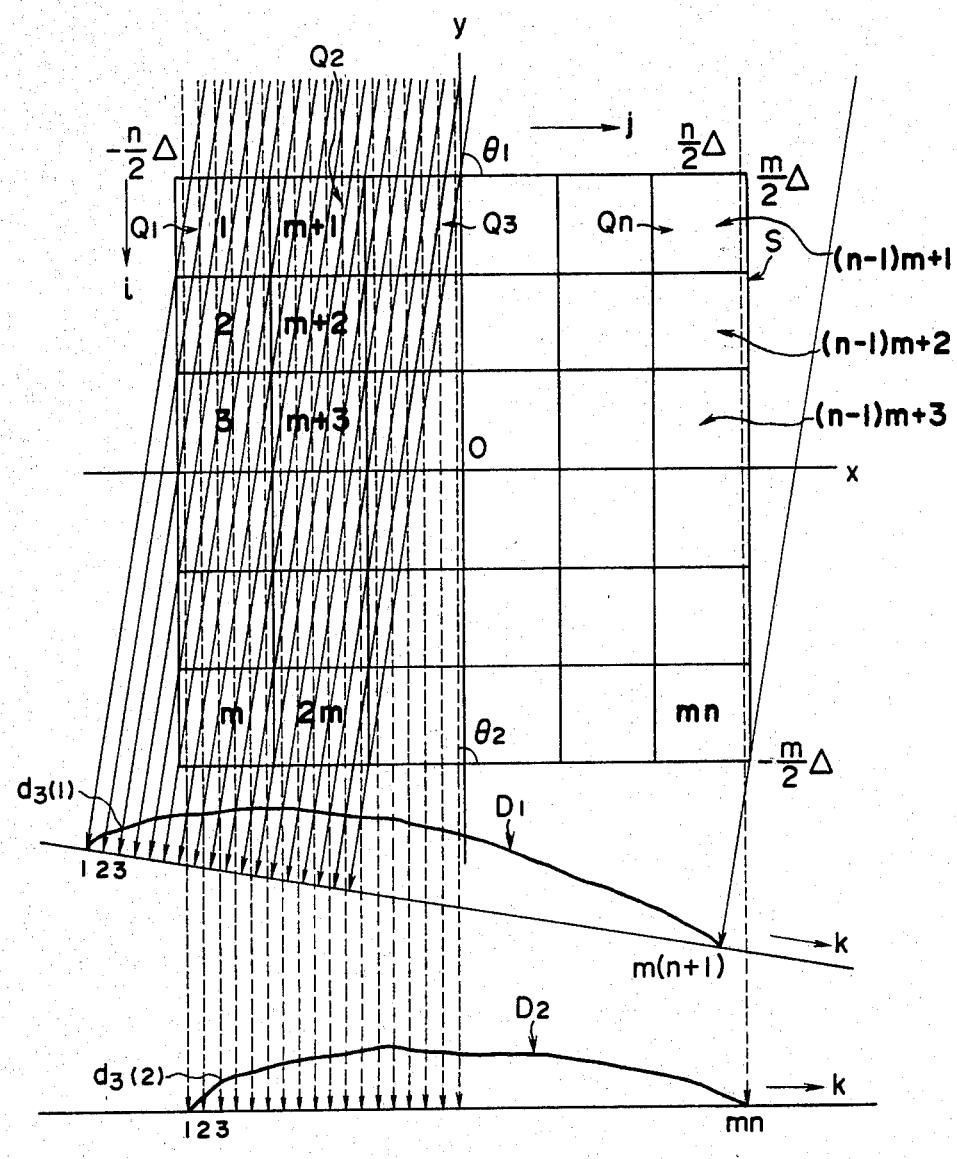
FIG. 13 is a schematic illustration for showing a reconstruction method of X-ray computed tomography in a tenth preferred embodiment of the present invention.

FIG. 13 is a schematic view illustrating a reconstruction method of an X-ray computed tomography of a tenth preferred embodiment of the present invention wherein the similar numbers in FIG. 13 substantially correspond to that of FIGS. 2 to 12.

In the tenth preferred embodiment, it is possible to produce a set of n of the groups of the measured values constituted by the measured values produced at each of the number of 2m of the positions properly spaced apart with respect to each other in sequence from one end of the first projectional distribution of X-rays $D_1$ to the other end thereof and to produce a set n of the groups of the measured values constituted by the measured values produced at each of the number of 2m the positions properly spaced apart from each other in sequence from one end of the second projectional distribution of X-ray $D_2$ to the other end thereof in reference to the first and second projectional distributions of X-rays $D_1$ and $D_2$ produced by projecting X-rays to the X-ray tested tissue B in a plurality of the desired (two) directions by the first means constituted by the measuring apparatus for projectional distribution of X-ray E and A/D converter E' etc., further, data output (digital signal) for each of the groups of the measured values obtained from the first means is fed in sequence to the transformer for the projectional distribution F constituting the second means, respectively.

This transformer for the projectional distribution F may produce by calculation and processing the signals corresponding to each of the X-ray absorption coefficients (two-dimensional data) of each of the picture elements in a set of n of the groups of picture elements constituted by the number of u ($=m<2m$) the picture elements in reference to the data output for each of the groups of the measured value from the first means, that is, the first data output of projectional distribution of X-ray (one-dimensional data; major data) and the second data output of the projectional distribution of X-ray (one-dimensional data; sub-data) corresponding to the first data output of projectional distribution of X-ray. As its practical or actual example, a digital computer storing the desired programs may be applied.

It will be described as follows a method in which each of the X-ray absorption coefficients (two-dimensional data) of the number of mn the picture elements constituting a pseudo-tomographic plane S (this plane S is constituted by a set of n the groups of picture elements) containing a tomography of the X-ray tested tissue B is calculated in reference to each of the groups of the measured values constituted by the number of 2m the measured values $d_k(1)$ (one-dimensional data) on the first projectional distribution of X-rays $D_1$ produced by the first means as the major data and each of the groups of the measured values (provided that the number of the measured values in the n-th group of the measured values is m) constituted by the number 2m of the measured values $d_k(2)$ (one-dimensional data) on the second projectional distribution of X-ray $D_2$ produced similarly by the first means.

At first, it is assumed that the pseudo-tomographic plane S applied as a tomography reconstruction plane of the X-ray tested tissue of body B is constituted such that the groups of picture elements applied as a partial plane of columns for the reconstruction of tomography constituted by the number of m of the small divided picture elements, as shown in FIG. 13, are collected to form a set n and a center of the plane S is set at an origin of x-y coordinates.

Also, it is assumed that for the sake of convenience of description, m and n are even numbers and a size of one picture element is a square of $\Delta \times \Delta$.

Further, it is assumed that X-ray beams passing through the pseudo-tomographic plane S are projected in parallel from two directions fulfilling a relation of $\theta_1 = \tan^{-1} m$ and $\theta_2 = \pi/2$ and a beam diameter of each of the unit X-ray beams is sufficiently small compared to that of each of the picture elements.

At first, in order to calculate the X-ray absorption coefficients $\mu_1$ to $\mu_m$ for each of the picture elements 1 to m in the first group of picture elements $Q_1$, the following equation may be provided if the number of $v_1$ ($=2m$) of the first projectional densities $d_1(1)$ to $d_{2m}(1)$ and the number of 2m of the second projectional densities $d_2(2)$ to $d_{2m}(2)$ are employed.

$$\mathbb{L}_{AP}\mu = \mathbb{D}_{AQ1} \qquad \qquad \ldots\ldots\ldots (31)$$

$$\mathbb{L}_{AP} = \begin{Bmatrix} \begin{matrix} 1 & & & & & & & & & & & & & \\ 1 & 1 & & & & & & & & & & & & \\ 1 & 1 & 1 & & & & & & & & & & & \\ & & & \ddots & & & & 0 & & & & & & \\ & & & & & & & & & & & & & \\ 1 & \cdot & \cdot & \cdot & \cdot & \cdot & 1 & & & & & & & \\ & 1 & \cdot & \cdot & \cdot & \cdot & \cdot & 1 & & & & & & \\ & & 1 & \cdot & \cdot & \cdot & \cdot & \cdot & 1 & & & & & \\ & & & 1 & \cdot & \cdot & \cdot & \cdot & \cdot & 1 & & & & \\ & & & & & \ddots & & & & & & & & \\ & & 0 & & & & & & & & & & & \\ & & & & & & & & & & & & & \\ & & & & & & 1 & \cdot & \cdot & \cdot & \cdot & \cdot & 1 & \\ 1 & \cdot & \cdot & \cdot & \cdot & \cdot & \cdot & \cdot & \cdot & \cdot & \cdot & \cdot & 1 & \\ 1 & \cdot & \cdot & \cdot & \cdot & \cdot & \cdot & \cdot & \cdot & \cdot & \cdot & \cdot & 1 & \\ 1 & \cdot & \cdot & \cdot & \cdot & \cdot & \cdot & \cdot & \cdot & \cdot & \cdot & \cdot & 1 & \\ & & & & & & & & & & & & & \\ 1 & \cdot & \cdot & \cdot & \cdot & \cdot & \cdot & \cdot & \cdot & \cdot & \cdot & \cdot & 1 & \\ 1 & \cdot & \cdot & \cdot & \cdot & \cdot & \cdot & \cdot & \cdot & \cdot & \cdot & \cdot & 1 & \end{matrix} \end{Bmatrix}$$

(with dimensions: $m$ rows for upper block, columns labeled $m$, $2m$; rows labeled $2m$, $2m+1$, $4m$; width $2m$)

$$\ldots\ldots (32)$$

$$\mu = (\mu_1, \mu_2, \mu_3, \ldots, \mu_{2m})^T$$

$$\mathbb{D}_{AQ1} = (d_1(1)/\alpha, d_2(1)/\alpha, \ldots, d_{2m}(1)/\alpha,$$
$$d_1(2), d_2(2), \ldots, d_{2m}(2))^T$$

and $\mathbb{L}_{AP}$ is a matrix of $4m \times 2m$.

$\alpha$ is a length of X-ray beams passing through one picture element in the directions $\theta_1$ and fulfills a relation of $$\alpha = \Delta \sqrt{1 + \cot^2 \theta_1}$$

and a symbol T is a transposition.

Resolving the equation (31) by a method of least squares may enable a calculation of the X-ray absorption coefficients $\mu_1$ to $\mu_{2m}$ of each of the picture elements 1 to 2m in the first group of picture elements $Q_1$.

However, in general, the data contain some measuring errors, thus when an answer for making an object function of $$F = \sum_{k=1}^{4m} r_k \qquad (33)$$

minimum is calculated by a mathematical programming under an equation of restrictive condition substantially the same as that of the equation (3) by introducing the non-negative correction values $r_1, r_2, r_3 \ldots r_{4m}$, resulting in that the most suitable two-dimensional data $\mu_1$ to $\mu_{2m}$ may be calculated after a limited times of calculation.

Provided that the suffix i of $l_{i,j}, \mu_j, r_i, p_i$ in the equation (3) is 1, 2, 3, ... 4m, and the suffix j is 1, 2, 3 ... 2m.

In the above example, the two-dimensional data $\mu_1$ to $\mu_{2m}$ have been calculated in reference to the object function for making a sum of absolute values of correction values in the equation of restrictive conditions minimum, there is also another method in which the object function of the above described equation (6) is made to be a minimum on the basis of the equation of restrictive condition being substantially the same as that of the equation (5).

Also provided in this case that the suffix i of $l_{i,j}, \mu_j, p_i$ in said equation (5) is 1, 2, 3 ..., 4m, and the suffix j is 1, 2, 3 ... 2m.

In reference to this, two-dimensional tomographic data $\mu_1$ to $\mu_{2m}$ of the X-ray tested tissue B are calculated under such conditions as the maximum correction value of the absolute value in the equation of restrictive conditions is minimum.

Further, it is possible to perform a calculation either by a method for making an object function of $$F = \sum_{k=1}^{4m} r_k^2 \quad (34)$$

minimum under an equation of restrictive condition of the preferred embodiment corresponding to the equation (3) or by a method for making an object function of $$F = r^2 \quad (35)$$

minimum under an equation of restrictive condition of the preferred embodiment corresponding to the equation (5).

The first number m of the two-dimensional data $\mu_1$ to $\mu_{2m}$ thus obtained, that is, only the data $\mu_1$ to $\mu_m$ are transmitted to the memory for three-dimensional internal structure G applied at a memory means, respectively.

Employing the number of $v_2(=v_1=2m)$ of the first projectional densities $d_{m+1}(1)$ to $d_{3m}(1)$, the number 2m of the second projectional densities $d_{m+1}(2)$ to $d_{3m}(2)$ and thus obtained X-ray absorption coefficient in order to calculate the X-ray absorption coefficients $\mu_{m+1}$ to $\mu_{2m}$ of each of the picture elements (m+1) to 2m in the second group of picture elements $Q_2$ may enable a calculation of the number of 2m of the X-ray absorption coefficients $\mu_{m+1}$ to $\mu_{3m}$ substantially in the same manner as said described ones.

In this way, the two-dimensional data $\mu_{m+1}$ to $\mu_{3m}$ are calculated, only the first number m of these two-dimensional data $\mu_{m+1}$ to $\mu_{3m}$, that is, only the data $\mu_{m+1}$ to $\mu_{2m}$ are transmitted to the memory G.

The X-ray absorption coefficient of each of the picture elements in the subsequent third to n-th groups of picture elements $Q_3$ to $Q_n$ may be calculated by repeating the substantial same operation in sequence and only the first number of m of the two-dimensional data of them are transmitted in sequence to the memory G.

Then, the memory for the three dimensional internal structure G is made such that each of the groups $Q_1$ to $Q_n$ of the picture elements is assembled in accordance with their relative orders after receiving the number m of signals from the dimensional transformer of projectional data F, that is, the groups of picture element of the order of the first to n-th are assembled from the left side thereof in accordance with their order and thereby the signals from the dimensional transformer of projectional data F may be stored, and also the data of three dimensional internal structure of the X-ray tested tissue B are calculated.

That is, the two-dimensional data $\mu_1$ to $\mu_{mn}$ transmitted in sequence by the number of m from the dimensional transformer of projectional data F are related to that of a certain section of the X-ray tested tissue of body B, another projectional distributions of X-ray $D_1'$, $D_2'$ may be produced by changing a measuring point by the measuring apparatus for projectional distribution of X-ray E, and thereby the two-dimensional data $\mu_1'$ to $\mu_{mn}'$ relating to other sections may easily be produced substantially in the same manner as that described above, so that it is possible to store the three dimensional internal structure of the X-ray tested tissue of body B by accumulating the two-dimensional data $\mu_1$ to $\mu_{mn}, \mu_1'$ to $\mu_{mn}', \mu_1''$ to $\mu_{mn}'' \ldots$ relating to several different sections. However, in order to construct a complete three-dimensional internal structure, it becomes necessary to have an interpolation etc. between each of the section data, so that the memory G may be used as a memory device having a calculation function for it.

Further, it is also the same as that of each of the preferred embodiments that to the memory G are connected the display of computed tomography of arbitrary transverse section J via the computed tomography reconstruction apparatus of arbitrary transverse section H, the improving apparatus for image quality of arbitrary transverse section I and D/A converter F'.

In order to produce a tomography of the X-ray tested tissue of body B by applying the above described arrangement, the first one-dimensional data (major data) $d_k(1)$ of the first projectional distribution of X-ray $D_1$ detected by X-ray detector C by projecting at first X-ray from X-ray source A in a desired direction $\theta_1$ to the X-ray tested tissue B is calculated by measuring each of the values $d_k(1)$ at the number of m(n+1) of the positions equally spaced apart with each other by a space w from one end of said first projectional distribution of X-ray $D_1$ up to the other end of said first projectional distribution of X-ray $D_1$ by using the measuring apparatus for projectional distribution of X-ray E, and at the same time the second one-dimensional data (sub-data) $d_k(2)$ of the second projectional distribution of X-ray $D_2$ detected by X-ray detector C by emitting or projecting X-ray from X-ray source A in a desired direction $\theta_2$ to the X-ray tested tissue B is calculated by measuring each of the values $d_k(2)$ at the number of mn of the positions equally spaced apart with each other by a space w from one end of said second projectional distribution of X-ray $D_2$ up to the other end of said second projectional distribution of X-ray $D_2$ by using the measuring apparatus for projection distribution of X-rays E.

Then, these one-dimensional data $d_k(1), d_k(2)$ are properly converted from their analogue form to digital form, the X-ray absorption coefficient of each of the picture elements is calculated for each of the groups of one set of the number 2m by the dimensional transformer of projectional data F with the above described method, then only the first number of m of X-ray absorption coefficients data for each of the groups of the picture elements are transmitted in sequence to the memory G and thereby each of the X-ray absorption coefficients $\mu_1$ to $\mu_{mn}$ (two-dimensional data) of the number of mn of the picture elements in the pseudo-tomographic plane S is calculated, and these X-ray absorption coefficients are stored in a specified sequence in the memory G.

Thereafter, these two-dimensional data $\mu_1$ to $\mu_{mn}$ are reconstructed and displayed as a tomogram of the X-ray tested tissue B by the display of computed tomography of arbitrary transverse section J from the memory G via computed tomography reconstruction apparatus of arbitrary transverse section H, the improving apparatus for image quality of arbitrary transverse section I and D/A converter F'.

Figure 14:
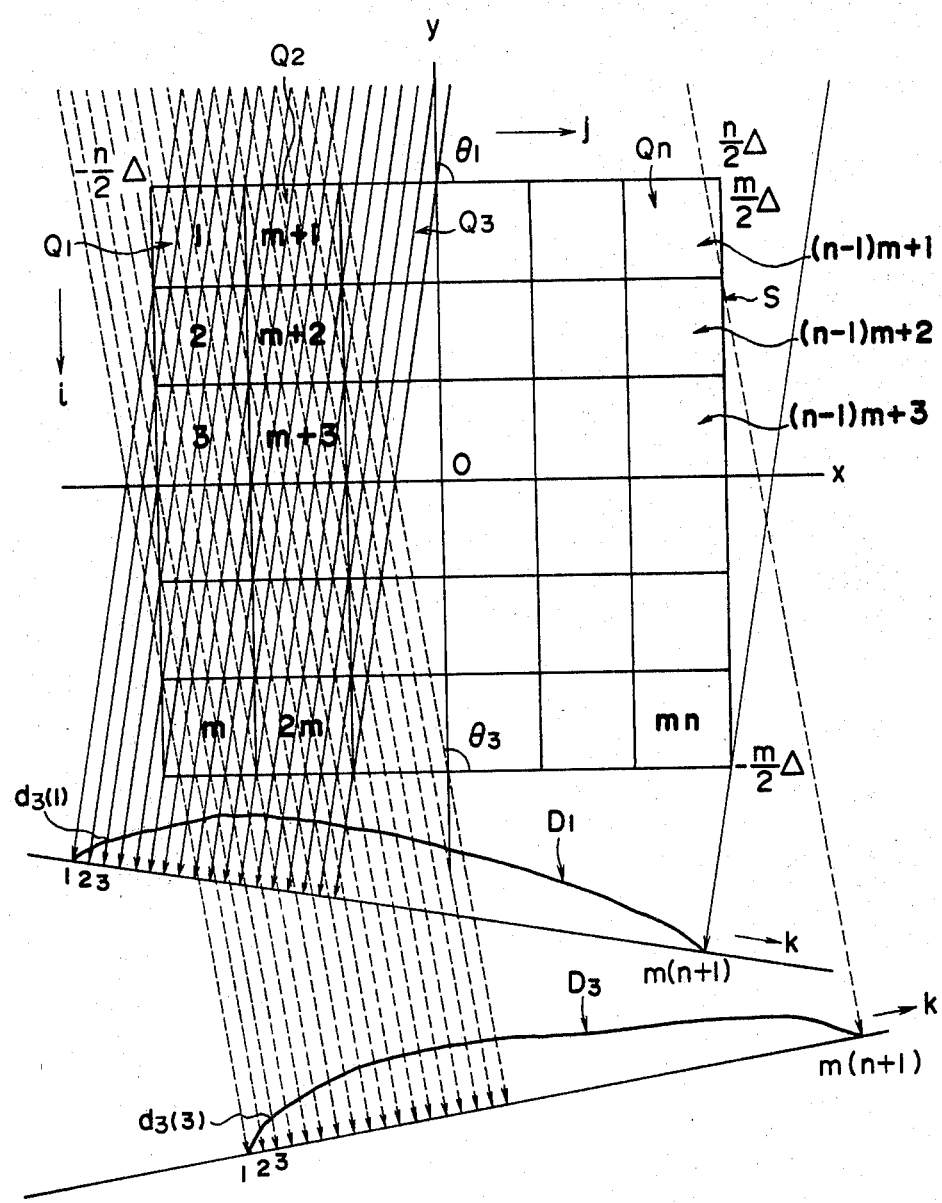
FIG. 14 is a schematic illustration for showing a reconstruction method of X-ray computed tomography in an eleventh preferred embodiment of the present invention.

FIG. 14 is a schematic view for illustrating a reconstruction method of X-ray computed tomography of an eleventh preferred embodiment of the present invention wherein the similar numbers in FIG. 14 substantially correspond to that of FIGS. 2 to 13.

In the eleventh preferred embodiment of the present invention, it is assumed that the pseudo-tomographic plane S (this pseudo-tomographic plane S is constituted by a set of n of the groups of picture elements constituted by the number m of the picture elements) applied as a tomography reconstruction plane of the X-ray tested tissue B is constituted by the number of mn of the picture elements 1 to mn divided into some small sections as shown in FIG. 14 and a center of the plane S is set at an origin of x-y coordinates.

Also, it is assumed that for the sake of convenience of description, m and n are even numbers and a size of one picture element is a square of $\Delta \times \Delta$.

Further, it is assumed that X-ray beams passing through the pseudo-tomographic plane S are projected by the number of m(n+1) in parallel from two-directions fulfilling a relation of $\theta_1 = \tan^{-1} m$ and $\theta_2 = -\tan^{-1} m$ and a beam diameter of each of the unit X-ray beams is sufficiently small compared to that of each of the picture elements.

Employing the number of 2m of the projectional densities $d_1(1)$ to $d_{2m}(1)$ projected in a direction of $\theta_1$ and the number of 2m of the projectional densities $d_1(3)$ to $d_{2m}(3)$ projected in a direction of $\theta_3$ in order to calculate the X-ray absorption coefficients $\mu_1$ to $\mu_m$ of each of the picture elements 1 to m in the first group of picture elements $Q_1$ may enable a provision of the following equation.

$$\mathbb{L}'_{AP} \mu = \mathbb{D}'_{AQ_1} \quad \ldots \ldots (36)$$

where, $$\mathbb{L}'_{AP} = \text{[matrix]} \quad \ldots \ldots (37)$$

$$\mu = (\mu_1, \mu_2, \mu_3, \ldots, \mu_{2m})^T$$

$$\mathbb{D}'_{AQ1} = (d_1(1), d_2(1), \ldots, d_{2m}(1), d_1(3), d_2(3), \ldots, d_{2m}(3))^T/\alpha$$

$L_{AP}$ is a matrix of $4m \times 2m$.

A value of $\alpha$ is a length of X-ray beams passing through one picture element in the directions $\theta_1$ and $\theta_3$, and fulfills a relation of $$\alpha = \Delta\sqrt{1 + \cot^2\theta_1} = \Delta\sqrt{1 + \cot^2\theta_3}$$

and a symbol T indicates a transposition.

Resolving the equation (36) by a method of least squares may enable a calculation of the two-dimensional tomographic data $\mu_1$ to $\mu_{2m}$ of the X-ray tested body tissue B substantially in the same manner as that of said embodiments. However, in general, the data contain some measuring errors, so that the errors in case of performing a reconstruction operation may be made a minimum by applying a mathematical programming substantially in the same manner as that of the above described preferred embodiments.

The signals corresponding to the first number of m of the X-ray absorption coefficients $\mu_1$ to $\mu_m$ in the X-ray absorption coefficients $\mu_1$ to $\mu_{2m}$ thus obtained as two-dimensional data are transmitted to the memory G.

Then, the number of 2m of the X-ray absorption coefficients for the second to n-th groups of picture elements $Q_2$ to $Q_n$ are calculated, only the first number of m of these X-ray absorption coefficients are transmitted to the memory G, and the X-ray absorption coefficients may be stored in the memory G in accordance with the specified order.

Then, these two-dimensional data $\mu_1$ to $\mu_{mn}$ are reconstructed and displayed from the memory G as the tomography of the X-ray tested body tissue B by the display of computed tomography of an arbitrary transverse section J via the computed tomography reconstruction apparatus of arbitrary transverse section H, the improving apparatus for image quality of arbitrary transverse section I and D/A converter F'.

Figure 15:
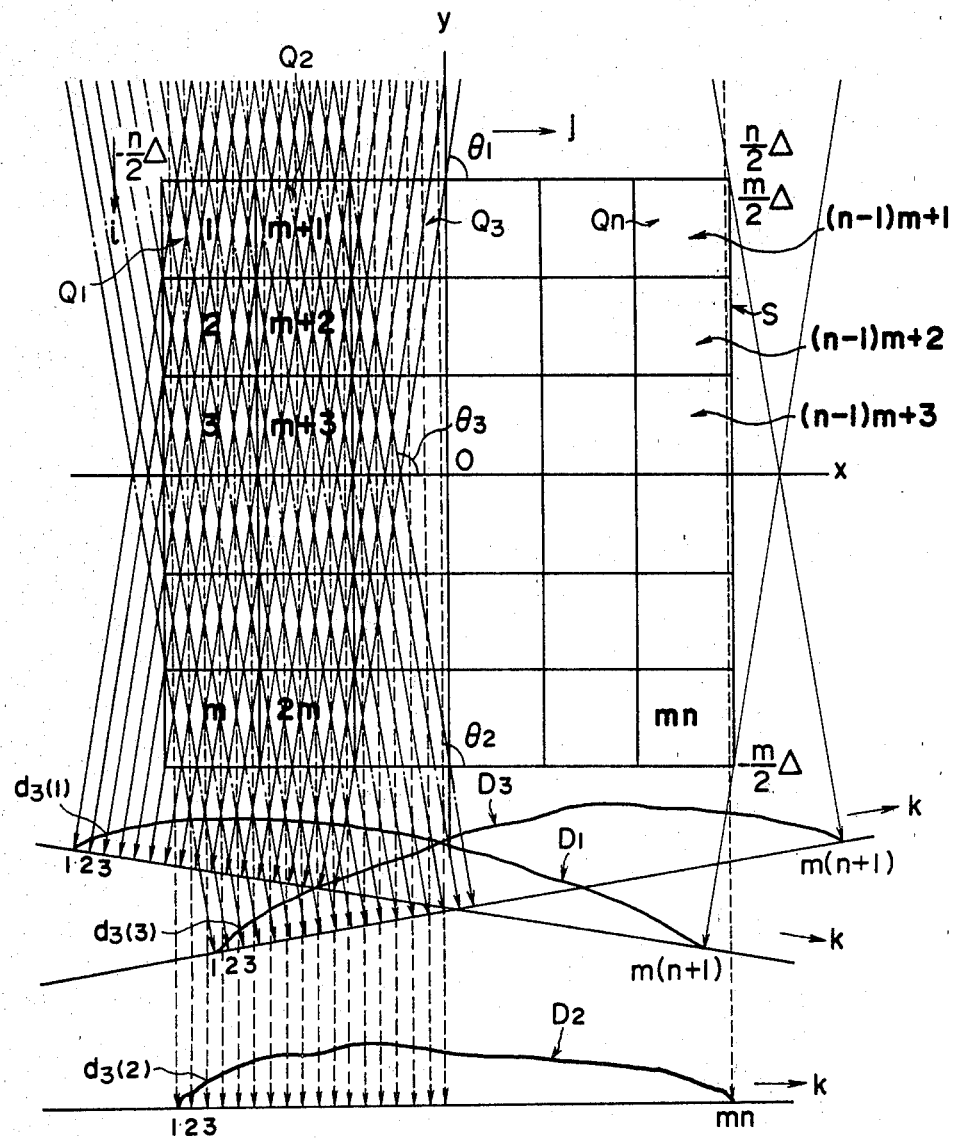
FIG. 15 is a schematic illustration for showing a reconstruction method of X-ray computed tomography in a twelveth preferred embodiment of the present invention.

FIG. 15 is a schematic view for illustrating a reconstruction method of X-ray computed tomography of a twelfth preferred embodiment of the present invention wherein the similar numbers in FIG. 15 substantially correspond to that of FIGS. 2 to 14.

Also in the twelfth preferred embodiment of the present invention, it is assumed that the pseudo-tomographic plane S as a reconstruction plane of the tomography of the X-ray tested body tissue B (this plane S is made of a set of n of the groups of picture elements constituted by the number of m of the picture elements) is constituted by the number mn of the small divided picture elements 1 to mn, as illustrated in FIG. 15, a center of the plane S is placed at an origin of x-y coordinates, the numbers m and n are even numbers for a convenience of description, and a size of one picture element is a square of $\Delta \times \Delta$.

Further, it is assumed that the X-ray beams passing through the pseudo-tomographic plane S are projected in parallel from three directions fulfilling a relation of $\theta_1 = \tan^{-1} m$, $\theta_2 = \pi/2$ and $\theta_3 = -\tan^{-1} m$ by the number of m(n+1), mn and m(n+1), respectively.

And further it is assumed that a beam diameter of each of the unit X-ray beams is sufficiently small compared to that of each of the picture elements.

Employing the number of 2m of the projectional densities $d_1(1)$ to $d_{2m}(1)$ projected from the direction $\theta_1$, the number of 2m of the projectional densities $d_1(2)$ to $d_{2m}(2)$ projected from the direction $\theta_2$ and the number of 2m of the projectional densities $d_1(3)$ to $d_{2m}(3)$ in order to calculate the X-ray absorption coefficients $\mu_1$ to $\mu_m$ of each of the picture elements 1 to m in the first group of picture elements $Q_1$ may enable a provision of the following equation.

$$\mathbb{L}''_{AP}\mu = \mathbb{D}''_{AQ1} \quad \ldots (38)$$

where, $$\mathbb{L}''_{AP} = \begin{pmatrix} \text{(matrix as shown)} \end{pmatrix} \quad \ldots (39)$$

$$\mu = (\mu_1, \mu_2, \mu_3, \ldots, \mu_{2m})^T$$

$$\mathbb{D}''_{AQ1} = (d_1(1)/\alpha, d_2(1)/\alpha, \ldots, d_{2m}(1)/\alpha,$$

$$d_1(2), d_2(2), \ldots, d_{2m}(2),$$

$$d_1(3)/\alpha, d_2(3)/\alpha, \ldots, d_{2m}(3)/\alpha)^T$$

$L_{AP}$ is a matrix of $6m \times 2m$.

A value of $\alpha$ is a length of X-ray beams passing through one picture element in the directions $\theta_1$ and $\theta_3$, and fulfills a relation of $$\alpha = \Delta\sqrt{1 + \cot^2\theta_1} = \Delta\sqrt{1 + \cot^2\theta_3}$$

and a symbol T indicates a transposition.

Resolving the equation (38) by a method of least squares may enable a calculation for the two-dimensional tomographic data $\mu_1$ to $\mu_{2m}$ of the X-ray tested tissue of body B substantially in the same manner as that of said preferred embodiments. However, in general, the data have some measuring errors, so that the errors found in case of performing a reconstruction are reduced to a minimum by applying a mathematical programming in the same manner as that of said preferred embodiments.

The signals corresponding to the first number of m of the X-ray absorption coefficients $\mu_1$ to $\mu_{2m}$ of the X-ray absorption coefficients $\mu_1$ to $\mu_{2m}$ applied as the two-dimensional data thus obtained are transmitted to the memory G.

In sequence, substantially in the same manner as above, the number of 2m of X-ray absorption coefficients are calculated for the second to n-th of the groups of picture elements $Q_2$ to $Q_n$, and further only the first number of m of these X-ray absorption coefficients are transmitted to the memory G, the X-ray absorption coefficients are stored in the memory G under the specified order.

Then, these two-dimensional data $\mu_1$ to $\mu_{mn}$ are reconstructed and displayed as a tomogram of the X-ray tested body tissue B by the display of computed tomography of arbitrary transverse section J from the memory G via computed tomography reconstruction apparatus of arbitrary transverse section H. the improving apparatus for image quality of arbitrary transverse section I and D/A converter F'.

As in the case of the tenth and eleventh preferred embodiments, it is also possible to construct a partial plane of columns for the tomography by combining properly the groups of picture elements constituted by the number 2m to m(n−1) of the picture elements in place of constructing a partial plane of columns of the tomography of the X-ray tested tissue of body B by each of the groups of picture elements constituted by the number of m of the picture elements.

Further, it may be possible to construct the groups of picture elements by the number m to m(n−1) of the picture elements in order to cause each of the groups of picture elements to form a partial plane of columns of the tomography and it may be possible to construct the groups of picture elements by the number of n to (m−1)n to form a partial plane of rows for the tomography.

Further, it is possible to construct each of the groups of picture elements by the number of picture elements fewer than the number m and n.

That is, one group of picture elements may be constructed by any number of picture elements if it is fewer than the number mn. However, it is preferable that the number of picture elements constituting one group of picture elements is defined to the proper number in reference to a capacity of the processing device for use in data processing and to the data processing time.

Further, when the groups of picture elements form a partial plane of rows of the tomography differing from that of the above described tenth and eleventh preferred embodiments, it is possible to apply some values of $\tan^{-1} n$, 0 or $\tan^{-1} n$, $-\tan^{-1} n$ as an example of two projectional directions and even in this case, it is possible to reconstruct a tomograph of the X-ray tested tissue of a body by calculating the number of mn (=N) the X-ray absorption coefficients substantially in the same manner as that of each of the above described preferred embodiments.

Further, when the groups of picture elements form a partial plane of columns of the tomography differing from that of the above described twelfth preferred embodiment, it is possible to apply some values of $\tan^{-1} n$, $-\tan^{-1} n$ and 0 as an example of three projectional directions and even in this case, it is possible to reconstruct a tomography of the X-ray tested tissue of a body by calculating the number of mn (=N) of the X-ray absorption coefficients substantially in the same manner as that of each of the above described preferred embodiments.

Further, it is possible to reconstruct a tomogram of the X-ray tested tissue of body in a similar manner even if the projecting direction shows more than three directions. However, when the number of projecting direction is increased more, an accuracy of forming the tomography may be improved, and to the contrary a data processing time is required more and hardware for the reconstruction system is made large, so that the number of projecting or emitting directions may be determined in reference to the above mentioned matters.

Further, it is possible to calculate the X-ray absorption coefficient applied as two-dimensional data in reference to each of the number 2m of one-dimensional data measured from one projectional distribution of X-rays and to each of a suitable number (which may be more than or less than the number of 2m) of one-dimensional data measured from the remaining projectional distributions of X-rays in place of the operations found in the tenth to twelfth preferred embodiments wherein each of the number of 2m of one-dimensional data is measured from one of a plurality of projectional distributions of X-rays and also each of the number of 2m of one-dimensional data is measured from the remaining projectional distributions of X-rays.

And in case of applying the projectional beams having their directions of $\pi/2$ or 0, each of the partial planes of column or each of the partial planes of row of pseudo-tomographic plane S is expressed by a mean value of the number of m or n of the beams, its object function may be added with a multiplication of m or n during its calculation process and in this case it is possible to save the capacity of memory or shorten a time of calculation.

What is claimed is:

1. A method of constructing a computed tomogram of the internal structure of an object analyzed by X-rays comprising, emitting toward an object being analyzed in a common direction relative to an imaginary reference direction and in a common tomographic plane a plurality of substantially parallel X-ray beams equally spaced from each other laterally, detecting and measuring the density of the individual X-ray beams at separate corresponding spaced points downstream of the object after traversing of the X-ray beams through said object and developing in dependence upon the measured density of said plurality of X-ray beams signals representative of and corresponding to the density of the individual X-ray beams measured, subsequently emitting toward said object from a different common direction relative to said reference direction in said common tomographic plane a second plurality of substantially parallel X-ray beams laterally equally spaced from each other and intersecting at individual regions in said object paths traversed by the first-mentioned plurality of X-ray beams, the areas of intersection having a matrix pattern, detecting and measuring the X-ray beam density of said second plurality individually at separate corresponding spaced points downstream of the object after the traversing of said beams through said object, developing signals in dependence upon the measured density of said individual second plurality of X-ray beams, calculating the absorption coefficient of each of the individual areas of the tomographic plane where the X-ray beam paths intersect with reference to said measured beam densities, each beam being no wider than the corresponding individual area of path intersections and for which the absorption coefficients are calculated, developing signals corresponding to calculated absorption coefficients, constructing with said signals a tomogram depicting an image of the internal structure of the object scanned and analyzed by said X-ray beams.

2. A method of constructing a tomogram of the internal structure of an object analyzed by X-rays according to claim 1, in which the tomograph comprises an image arranged in a matrix of image picture elements arranged in parallel columns and intersecting parallel rows arranged with respect to said imaginary reference direction.

3. A method of constructing a tomogram of the internal structure of an object analyzed by X-rays according to claim 1, in which said object is animal tissue.

4. A method of constructing a tomogram of an internal structure of an object according to claim 1, in which said object is living tissue.

5. A method of constructing a tomogram of the internal structure of an object analyzed by X-rays according to claim 1, in which the picture elements constitute N groups having rows (m) and columns (n), and in which the directions define the values of tan m and $\pi/2$ with respect to the reference direction.

6. A method of constructing a tomogram of the internal structure of an object analyzed by X-rays according to claim 1, in which the width of the X-ray beams is less than that of a corresponding picture element depicted therefrom.

7. A method of constructing a tomogram of the internal structure of an object analyzed by X-rays according to claim 1, in which said X-ray beams of each corresponding plurality are emitted simultaneously.

8. A method of constructing a tomogram of the internal structure of an object analyzed by X-rays according to claim 1, in which the density measurement values are stored before constructing of said image in said tomograph is effected.

9. A method of constructing a tomogram of the internal structure of an object analyzed by X-rays according to claim 1, in which a third plurality of X-rays beams is emitted toward said object in a third direction and density measurements are made thereof similarly to the first two mentioned directions and the three directions have the angular spacings relative to the reference direction having the values of $\tan^{-1} m$, $-\tan^{-1} m$ and $\pi/2$, and wherein the tomograph has rows (m) and columns (n) of the picture elements.

10. A method of constructing a tomogram of the internal structure of an object analyzed by X-rays according to claim 1, in which said tomogram has the picture elements arranged in parallel rows (m) and parallel columns (n), and the directions have the angular spacings relative to the reference direction at respective values of $\tan^{-1} m$ and $\pi/2$.

11. A method of constructing a tomogram of the internal structure of an object analyzed by X-rays according to claim 1, in which said tomogram has the picture elements arranged in parallel rows (m) and parallel columns (n) in a matrix arrangement in which (m) and (n) are positive integers greater than 1.

12. A method of constructing a tomogram of the internal structure of an object analyzed by X-rays according to claim 11, in which said positive integers are even numbers.

* * * * *